US008100869B2

(12) United States Patent
Vangsness et al.

(10) Patent No.: US 8,100,869 B2
(45) Date of Patent: Jan. 24, 2012

(54) MEDICAL VALVE WITH EXPANDABLE MEMBER

(75) Inventors: Todd S. Vangsness, Stow, MA (US);
Jeffrey F. Kane, Hudson, MA (US); Ian Kimball, Clinton, MA (US)

(73) Assignee: Nypro Inc., Clinton, MA (US)

( * ) Notice: Subject to any disclaimer, the term of this patent is extended or adjusted under 35 U.S.C. 154(b) by 536 days.

(21) Appl. No.: 11/837,417

(22) Filed: Aug. 10, 2007

(65) Prior Publication Data
US 2008/0039802 A1 Feb. 14, 2008

Related U.S. Application Data

(60) Provisional application No. 60/837,400, filed on Aug. 11, 2006.

(51) Int. Cl.
*A61M 5/00* (2006.01)
*F16L 37/28* (2006.01)
(52) U.S. Cl. .................. 604/249; 251/149.2; 251/149.6
(58) Field of Classification Search .................. 604/158, 604/160–162, 164.01, 164.02, 167.02–167.04, 604/246, 249; 251/149.1–149.9
See application file for complete search history.

(56) References Cited

U.S. PATENT DOCUMENTS

| 2,594,405 | A | 4/1952 | Deters ............................. 137/53 |
| 2,693,801 | A | 11/1954 | Foreman ........................ 128/214 |
| 2,705,501 | A | 4/1955 | Frizsch et al. ................. 137/113 |
| 3,087,492 | A | 4/1963 | Garth ............................. 128/350 |
| 3,105,511 | A | 10/1963 | Murphy, Jr. .................... 137/399 |
| 3,192,949 | A | 7/1965 | De See ........................... 137/540 |
| 3,385,301 | A | 5/1968 | Harautuneian ................ 128/349 |
| 3,399,677 | A | 9/1968 | Gould et al. ................... 128/349 |
| 3,416,567 | A | 12/1968 | Von Dardel et al. .......... 137/604 |
| 3,538,950 | A | 11/1970 | Porteners ....................... 137/608 |
| 3,570,484 | A | 3/1971 | Steer .............................. 128/214 |
| 3,572,375 | A | 3/1971 | Rosenberg ..................... 137/512 |
| 3,806,086 | A | 4/1974 | Cloyd ........................... 251/149.7 |
| 3,831,629 | A | 8/1974 | Mackal et al. ................. 137/525 |
| 3,838,843 | A | 10/1974 | Bernhard ...................... 251/149.1 |
| 3,923,065 | A | 12/1975 | Nozick et al. ................. 128/348 |
| 3,965,910 | A | 6/1976 | Fischer ........................ 128/349 R |
| 3,994,293 | A | 11/1976 | Ferro ........................... 128/214 R |
| 4,063,555 | A | 12/1977 | Ulinder ....................... 128/214 R |
| 4,080,965 | A | 3/1978 | Phillips ....................... 128/214 D |
| 4,116,201 | A | 9/1978 | Shah ............................. 128/351 |
| 4,121,585 | A | 10/1978 | Becker, Jr. .................. 128/214 R |
| 4,143,853 | A | 3/1979 | Abramson ................... 251/149.1 |
| 4,223,808 | A | 9/1980 | Williams et al. ................ 222/88 |
| 4,324,239 | A | 4/1982 | Gordon et al. .............. 128/214 R |

(Continued)

FOREIGN PATENT DOCUMENTS

EP 0268480 A1 5/1988

(Continued)

*Primary Examiner* — Jackie Ho
*Assistant Examiner* — William Carpenter
(74) *Attorney, Agent, or Firm* — Sunstein Kann Murphy & Timbers LLP

(57) ABSTRACT

A medical valve transitions between an open mode that permits fluid flow, and a closed mode that prevents fluid flow. To that end, the valve has a housing with an inlet and an outlet, and actuator moveable distally within the housing. The medical valve also has a resilient member with an aperture. The distal movement of the actuator opens the aperture within the resilient member, thereby transitioning the medical valve from the open to the closed mode.

36 Claims, 23 Drawing Sheets

U.S. PATENT DOCUMENTS

| | | | | |
|---|---|---|---|---|
| 4,334,551 | A | 6/1982 | Pfister | 137/614.03 |
| 4,344,435 | A | 8/1982 | Aubin | 128/350 R |
| 4,387,879 | A * | 6/1983 | Tauschinski | 251/149.1 |
| 4,421,296 | A | 12/1983 | Stephens | 251/149.7 |
| 4,496,348 | A | 1/1985 | Genese et al. | 604/167 |
| 4,498,658 | A | 2/1985 | Mikiya | 251/149.6 |
| 4,535,820 | A | 8/1985 | Raines | 137/854 |
| 4,585,435 | A | 4/1986 | Vaillancourt | 604/27 |
| 4,596,557 | A | 6/1986 | Pexa | 604/86 |
| 4,617,015 | A | 10/1986 | Foltz | 604/100 |
| 4,675,003 | A | 6/1987 | Hooven | 604/9 |
| 4,681,132 | A | 7/1987 | Lardner | 137/271 |
| 4,683,905 | A | 8/1987 | Vigneau et al. | 137/329 |
| 4,683,916 | A | 8/1987 | Raines | 137/854 |
| 4,710,168 | A | 12/1987 | Schwab et al. | 604/99 |
| 4,712,583 | A | 12/1987 | Pelmulder et al. | 137/852 |
| 4,743,235 | A | 5/1988 | Waldbillig et al. | 604/250 |
| 4,745,950 | A | 5/1988 | Mathieu | 137/798 |
| 4,752,287 | A | 6/1988 | Kurtz et al. | 604/99 |
| 4,752,292 | A | 6/1988 | Lopez et al. | 604/244 |
| 4,758,224 | A | 7/1988 | Siposs | 604/119 |
| 4,776,369 | A | 10/1988 | Lardner et al. | 137/515.5 |
| 4,809,679 | A | 3/1989 | Shimonaka et al. | 128/4 |
| 4,816,020 | A | 3/1989 | Brownell | 137/112 |
| 4,819,684 | A | 4/1989 | Zaugg et al. | 137/112 |
| 4,830,331 | A | 5/1989 | Vindum | 251/63 |
| 4,842,591 | A * | 6/1989 | Luther | 604/537 |
| 4,850,978 | A | 7/1989 | Dudar et al. | 604/201 |
| 4,874,377 | A | 10/1989 | Newgard et al. | 604/167 |
| 4,915,687 | A | 4/1990 | Sivert | 604/83 |
| 4,917,668 | A * | 4/1990 | Haindl | 604/167.03 |
| 4,935,010 | A | 6/1990 | Cox et al. | 604/122 |
| 5,006,114 | A | 4/1991 | Rogers et al. | 604/167 |
| 5,041,087 | A | 8/1991 | Loo et al. | 604/83 |
| 5,048,537 | A | 9/1991 | Messinger | 128/673 |
| 5,049,128 | A | 9/1991 | Duquette | 604/83 |
| 5,065,783 | A | 11/1991 | Ogle, II | 137/68.1 |
| 5,080,654 | A | 1/1992 | Picha et al. | 604/167 |
| 5,085,645 | A | 2/1992 | Purdy et al. | 604/167 |
| 5,100,394 | A | 3/1992 | Dudar et al. | 604/283 |
| 5,108,380 | A | 4/1992 | Herlitze et al. | 604/283 |
| 5,147,333 | A | 9/1992 | Raines | 604/249 |
| 5,171,230 | A | 12/1992 | Eland et al. | 604/250 |
| 5,190,067 | A * | 3/1993 | Paradis et al. | 137/1 |
| 5,199,947 | A | 4/1993 | Lopez et al. | 604/56 |
| 5,203,775 | A | 4/1993 | Frank et al. | 604/256 |
| 5,215,538 | A | 6/1993 | Larkin | 604/249 |
| 5,221,271 | A | 6/1993 | Nicholson et al. | 604/283 |
| 5,230,706 | A | 7/1993 | Duquette | 604/83 |
| 5,242,393 | A | 9/1993 | Brimhall et al. | 604/86 |
| 5,242,432 | A | 9/1993 | DeFrank | 604/284 |
| 5,269,771 | A | 12/1993 | Thomas et al. | 604/213 |
| 5,280,876 | A | 1/1994 | Atkins | 251/149.1 |
| 5,300,034 | A | 4/1994 | Behnke et al. | 604/167 |
| 5,320,328 | A | 6/1994 | Decloux et al. | 251/326 |
| 5,330,435 | A | 7/1994 | Vaillancourt | 604/167 |
| 5,349,984 | A | 9/1994 | Weinheimer et al. | 137/543.21 |
| 5,360,413 | A | 11/1994 | Leason et al. | 604/249 |
| 5,380,306 | A | 1/1995 | Brinon | 604/264 |
| 5,390,898 | A * | 2/1995 | Smedley et al. | 251/149.6 |
| 5,401,255 | A | 3/1995 | Sutherland et al. | 604/247 |
| 5,439,451 | A | 8/1995 | Collinson et al. | 604/247 |
| 5,456,675 | A * | 10/1995 | Wolbring et al. | 604/537 |
| 5,458,640 | A | 10/1995 | Gerrone | 604/264 |
| 5,465,938 | A * | 11/1995 | Werge et al. | 251/149.1 |
| 5,474,536 | A | 12/1995 | Bonaldo | 604/86 |
| 5,474,544 | A | 12/1995 | Lynn | 604/283 |
| 5,509,433 | A | 4/1996 | Paradis | 137/1 |
| 5,509,912 | A | 4/1996 | Vaillancourt et al. | 604/283 |
| 5,520,666 | A | 5/1996 | Choudhury et al. | 604/283 |
| 5,533,708 | A | 7/1996 | Atkinson et al. | 251/149.1 |
| 5,533,983 | A | 7/1996 | Haining | 604/249 |
| 5,535,785 | A * | 7/1996 | Werge et al. | 137/843 |
| 5,540,661 | A * | 7/1996 | Tomisaka et al. | 604/265 |
| 5,549,566 | A | 8/1996 | Elias et al. | 604/167 |
| 5,569,209 | A | 10/1996 | Roitman | 604/190 |
| 5,569,235 | A | 10/1996 | Ross et al. | 604/403 |
| 5,573,516 | A | 11/1996 | Tyner | 604/249 |
| 5,578,059 | A * | 11/1996 | Patzer | 604/249 |
| 5,613,663 | A * | 3/1997 | Schmidt et al. | 251/149.2 |
| 5,616,129 | A | 4/1997 | Mayer | 604/167 |
| 5,616,130 | A | 4/1997 | Mayer | 604/167 |
| 5,620,434 | A | 4/1997 | Brony | 604/406 |
| 5,674,206 | A | 10/1997 | Allton et al. | 604/249 |
| 5,676,346 | A | 10/1997 | Leinsing | 251/149.1 |
| 5,685,866 | A | 11/1997 | Lopez | 604/249 |
| 5,694,686 | A | 12/1997 | Lopez | 29/890.126 |
| 5,695,466 | A | 12/1997 | Lopez et al. | 604/93 |
| 5,699,821 | A | 12/1997 | Paradis | 137/1 |
| 5,700,248 | A | 12/1997 | Lopez | 604/249 |
| 5,730,418 | A | 3/1998 | Feith et al. | 251/149.6 |
| 5,749,861 | A | 5/1998 | Guala et al. | 604/249 |
| RE35,841 | E | 7/1998 | Frank et al. | 604/256 |
| 5,775,671 | A * | 7/1998 | Cote, Sr. | 251/149.8 |
| 5,806,831 | A | 9/1998 | Paradis | 251/149.1 |
| 5,820,601 | A | 10/1998 | Mayer | 604/167 |
| 5,921,264 | A | 7/1999 | Paradis | 137/15 |
| 5,957,898 | A | 9/1999 | Jepson et al. | 604/256 |
| 6,029,946 | A | 2/2000 | Doyle | 251/149.1 |
| 6,036,171 | A | 3/2000 | Weinheimer et al. | 251/149.1 |
| 6,039,302 | A | 3/2000 | Cote, Sr. et al. | 251/149.1 |
| 6,048,335 | A | 4/2000 | Mayer | 604/167 |
| 6,050,978 | A | 4/2000 | Orr et al. | 604/249 |
| 6,063,062 | A | 5/2000 | Paradis | 604/249 |
| 6,068,011 | A | 5/2000 | Paradis | 137/1 |
| 6,079,432 | A | 6/2000 | Paradis | 137/1 |
| 6,089,541 | A | 7/2000 | Weinheimer et al. | 251/149.6 |
| 6,142,446 | A | 11/2000 | Leinsing | 251/149.1 |
| 6,152,900 | A | 11/2000 | Mayer | 604/167 |
| 6,228,069 | B1 | 5/2001 | Barth et al. | 604/249 |
| 6,245,048 | B1 | 6/2001 | Fangrow, Jr. et al. | 604/249 |
| 6,290,206 | B1 | 9/2001 | Doyle | 251/149.1 |
| 6,344,033 | B1 | 2/2002 | Jepson et al. | 604/256 |
| 6,428,520 | B1 | 8/2002 | Lopez et al. | 604/249 |
| 6,543,745 | B1 | 4/2003 | Enerson | 251/149.7 |
| 6,595,964 | B2 | 7/2003 | Finley et al. | 604/246 |
| 6,595,981 | B2 * | 7/2003 | Huet | 604/523 |
| 6,609,696 | B2 | 8/2003 | Enerson | 251/86 |
| 6,669,673 | B2 | 12/2003 | Lopez | 604/249 |
| 6,695,817 | B1 | 2/2004 | Fangrow, Jr. | 604/167.01 |
| 6,916,309 | B2 | 7/2005 | Fangrow, Jr. | 604/167.01 |
| 7,004,934 | B2 | 2/2006 | Vaillancourt | 604/533 |
| 7,008,404 | B2 * | 3/2006 | Nakajima | 604/158 |
| 7,184,825 | B2 | 2/2007 | Leinsing et al. | 604/20 |
| 7,497,849 | B2 | 3/2009 | Fangrow, Jr. | 604/247 |
| 2001/0049508 | A1 | 12/2001 | Fangrow, Jr. et al. | 604/256 |
| 2002/0029020 | A1* | 3/2002 | Cote et al. | 604/247 |
| 2003/0050610 | A1 | 3/2003 | Newton et al. | 604/256 |
| 2003/0093061 | A1 | 5/2003 | Ganem | 604/533 |
| 2003/0098430 | A1 | 5/2003 | Leinsing et al. | 251/149.6 |
| 2003/0141477 | A1 | 7/2003 | Miller | 251/149.1 |
| 2004/0006330 | A1 | 1/2004 | Fangrow, Jr. | 604/533 |
| 2004/0049158 | A1* | 3/2004 | Ley et al. | 604/167.03 |
| 2004/0073171 | A1 | 4/2004 | Rogers et al. | 604/164.13 |
| 2005/0228362 | A1 | 10/2005 | Vaillancourt | 604/533 |
| 2006/0161115 | A1 | 7/2006 | Fangrow | 604/249 |
| 2006/0200072 | A1 | 9/2006 | Peppel | 604/93.01 |
| 2006/0211997 | A1 | 9/2006 | Fangrow | 604/246 |
| 2006/0211998 | A1 | 9/2006 | Fangrow | 604/246 |
| 2006/0211999 | A1 | 9/2006 | Fangrow | 604/246 |
| 2006/0264848 | A1 | 11/2006 | Fangrow | 604/249 |
| 2006/0270999 | A1 | 11/2006 | Fangrow | 604/249 |
| 2006/0271016 | A1 | 11/2006 | Fangrow | 604/539 |
| 2007/0112312 | A1 | 5/2007 | Fangrow | 604/246 |
| 2007/0112313 | A1 | 5/2007 | Fangrow | 604/246 |
| 2007/0218757 | A1 | 9/2007 | Guala | 439/589 |
| 2008/0172003 | A1 | 7/2008 | Plishka et al. | 604/249 |
| 2008/0172005 | A1 | 7/2008 | Jepson | 604/249 |
| 2008/0190485 | A1 | 8/2008 | Guala | 137/1 |

FOREIGN PATENT DOCUMENTS

| | | |
|---|---|---|
| EP | 0629418 A1 | 12/1994 |
| EP | 1243285 | 9/2002 |
| GB | 2079162 | 1/1982 |
| WO | WO 83/02559 | 8/1983 |
| WO | WO 93/11828 | 6/1993 |
| WO | WO 96/00107 | 1/1996 |

| | | | | | | |
|---|---|---|---|---|---|---|
| WO | WO 97/39791 | 10/1997 | | WO | WO 01/20218 A1 | 3/2001 |
| WO | WO 98/22178 | 5/1998 | | WO | WO 03/018104 A2 | 3/2003 |
| WO | WO 98/26835 | 6/1998 | | WO | WO 03/018105 A1 | 3/2003 |
| WO | WO 98/39594 | 9/1998 | | WO | WO 2004/060466 | 7/2004 |
| WO | WO 00/44433 | 8/2000 | | | | |

* cited by examiner

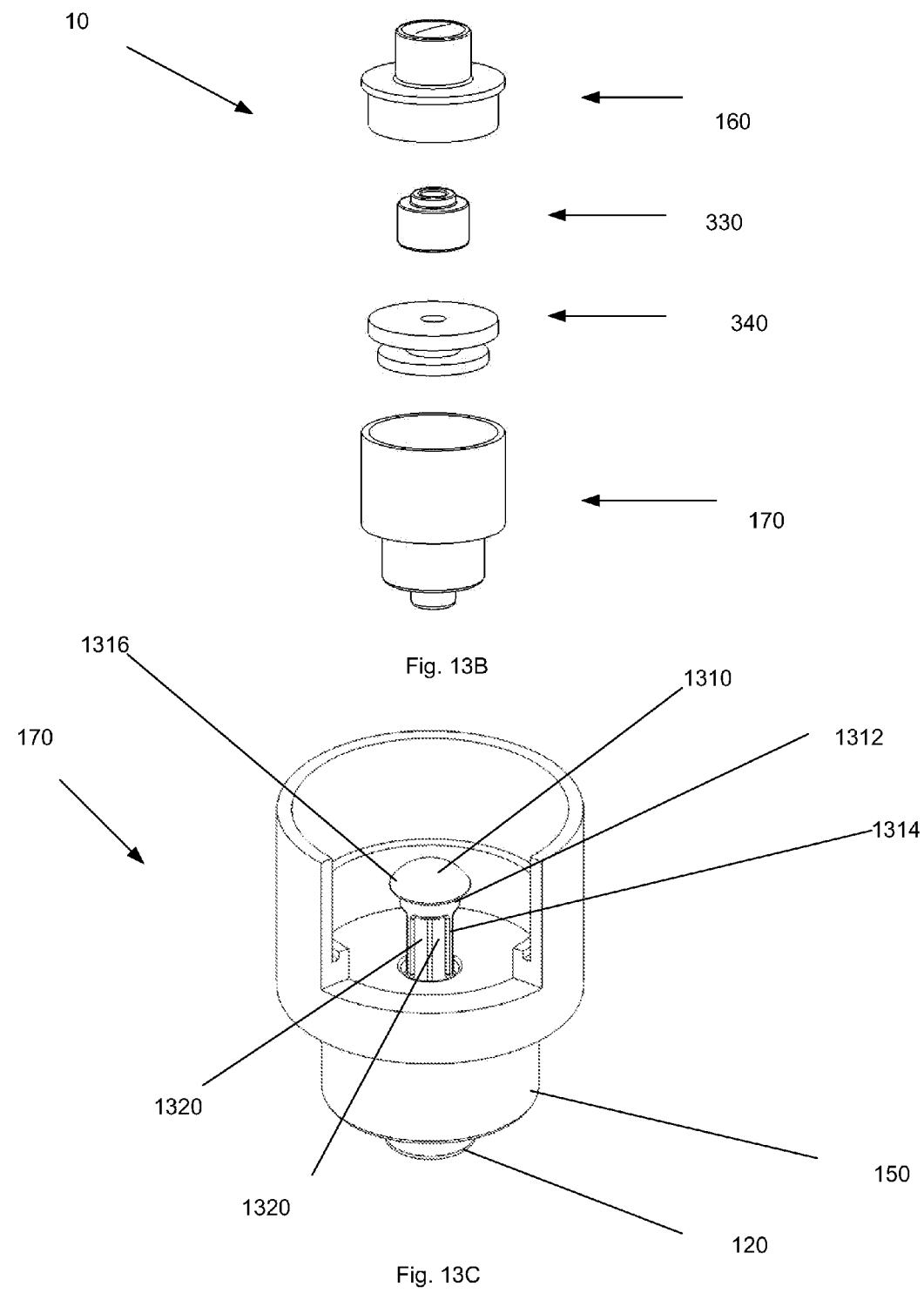

MEDICAL VALVE WITH EXPANDABLE MEMBER

PRIORITY

This patent application claims priority from provisional United States patent application:

U.S. Patent Application No. 60/837,400, filed Aug. 11, 2006, entitled, "Medical Valve with Expandable Member,", and naming Jeffrey F. Kane and Todd S. Vangsness as inventors, the disclosure of which is incorporated herein, in its entirety, by reference.

FIELD OF THE INVENTION

The invention generally relates to medical valves and, more particularly, the invention relates to mitigating fluid drawback through medical valves.

BACKGROUND

In general terms, medical valving devices often act as a sealed port that may be repeatedly accessed to non-invasively inject fluid into (or withdraw fluid from) a patient's vasculature. Consequently, a medical valve permits the patient's vasculature to be freely accessed without requiring such patient's skin be repeatedly pierced by a needle.

Medical personnel insert a medical instrument into the medical valve to inject fluid into (or withdraw fluid from) a patient who has an appropriately secured medical valve. Once inserted, fluid may be freely injected into or withdrawn from the patient. Problems can arise, however, when the medical instrument is withdrawn from the valve. Specifically, suction produced by the withdrawing medical instrument can undesirably cause blood to be drawn proximally into or toward the valve. In addition to coagulating and impeding the mechanical operation of the valve, blood in the valve also compromises the sterility of the valve.

SUMMARY OF THE INVENTION

In accordance with one embodiment of the present invention, a medical valve transitions between an open mode that permits fluid flow, and a closed mode that prevents fluid flow. The medical valve has a housing having an inlet and an outlet, an actuator, and a resilient member having an aperture that may or may not be self-sealing. For example, the aperture may be a pinhole or a slit. The actuator is moveable distally within the housing after insertion of a medical implement into the inlet. Distal movement of the actuator opens the aperture, thereby transitioning the valve from the closed to the open mode. Proximal movement of the actuator can close the aperture and transition the valve from the open to the closed mode. To aid in valve closing, the resilient member may proximally bias the actuator.

In some embodiments, the actuator may include a body portion, and a plurality of leg members extending from the body portion. The leg members may be connected to the body portion by a hinge that allows the leg members to flex or pivot with respect to the body portion. During distal movement of the actuator, the moveable leg members may flex radially outward and apply a radial force on the aperture, causing the aperture to open. Alternatively, some or all of the leg members can be stationary with respect to the body portion.

In accordance with other embodiments of the present invention, the resilient member can include a plurality of protrusions that cooperate with the stationary leg members. The protrusions may extend proximally, and the stationary leg members may engage the protrusions as the valve transitions from the closed mode to the open mode. By engaging the protrusions, the stationary leg members prevent the aperture from closing.

In accordance with still other embodiments, the medical valve may include a valve seat against which the resilient member may seal. The valve seat may be angled such that the resilient member deforms to the shape of the valve seat as the valve transitions from the closed to the open mode.

The medical valve may also have a swabbable member sealing the inlet. Among other things, the swabbable member may have a recloseable aperture there through.

Moreover, the housing may also include a plurality of protrusions extending proximally from the outlet. The protrusions prevent the aperture from closing as the valve transitions from the closed mode to the open mode.

In some embodiments, the medical valve may also include a plug member extending proximally, and passing through the aperture in the resilient member. The aperture and the plug member cooperate with one another to prevent flow through the valve in the closed mode. The plug member may have a lower portion distal to the resilient member and an upper portion proximal to the resilient member. The lower portion may have a plurality of channels for allowing fluid flow through the valve when in the open mode. The upper portion and the aperture may have similar cross-sectional geometries (e.g., they may both be circular, oval, etc.), and the resilient member may seal against the upper portion when in the closed mode.

In some embodiments, the actuator may include an actuator channel through it. Moreover, in other embodiments, the actuator may have a distally extending portion, and the resilient member may have a raised portion (e.g., a proximally extending portion) that extends into the actuator's distally extending portion. In such a configuration, the distally extending portion may provide a radially compressive force to the raised portion, and keep the aperture closed when the valve is in the closed mode. In some embodiments, the valve may produce a positive or substantially neutral fluid displacement at the outlet during disconnection of the medical implement.

In accordance with other embodiments, the actuator and the resilient member may be chemically bonded to one another to form a single internal valve mechanism. Additionally or alternatively, the actuator and the resilient member may be formed using a two-shot manufacturing process, thereby creating a single internal valve mechanism.

In accordance with another embodiment of the invention, a method connects a medical valve to a patient. Among other things, the medical valve has a housing with an inlet and an outlet, an actuator, and a resilient member. The method then inserts a medical implement through the inlet to contact the actuator, and moves the medical implement distally within the housing to move the actuator distally. The actuator's distal movement opens an aperture within the resilient member, causing the inlet and outlet to be in fluid communication. Finally, the method transfers fluid between the medical implement and the patient through the valve.

In some embodiments, the valve may form a longitudinally directed fluid channel between the inlet and the outlet when the actuator opens the aperture. The medical instrument may have a standard luer taper at its distal end. Additionally, transferring fluid can include injecting fluid from the medical implement to the patient, or removing fluid from the patient.

BRIEF DESCRIPTION OF THE DRAWINGS

The foregoing features of the invention will be more readily understood by reference to the following detailed description, taken with reference to the accompanying drawings, in which:

FIG. 13B schematically shows a perspective exploded view of the medical valve shown in FIG. 13A.

FIG. 13C schematically shows an illustrative embodiment of the outlet of the valve of FIG. 13A. This figure shows a section of the outlet cut-away to illustrate the proximally extending post member.

DESCRIPTION OF ILLUSTRATIVE EMBODIMENTS

In illustrative embodiments, a medical valve has an internal valve mechanism with an actuator member that is moveable to open an aperture in a resilient member. Details of illustrative embodiments are discussed below.

Figure 1:
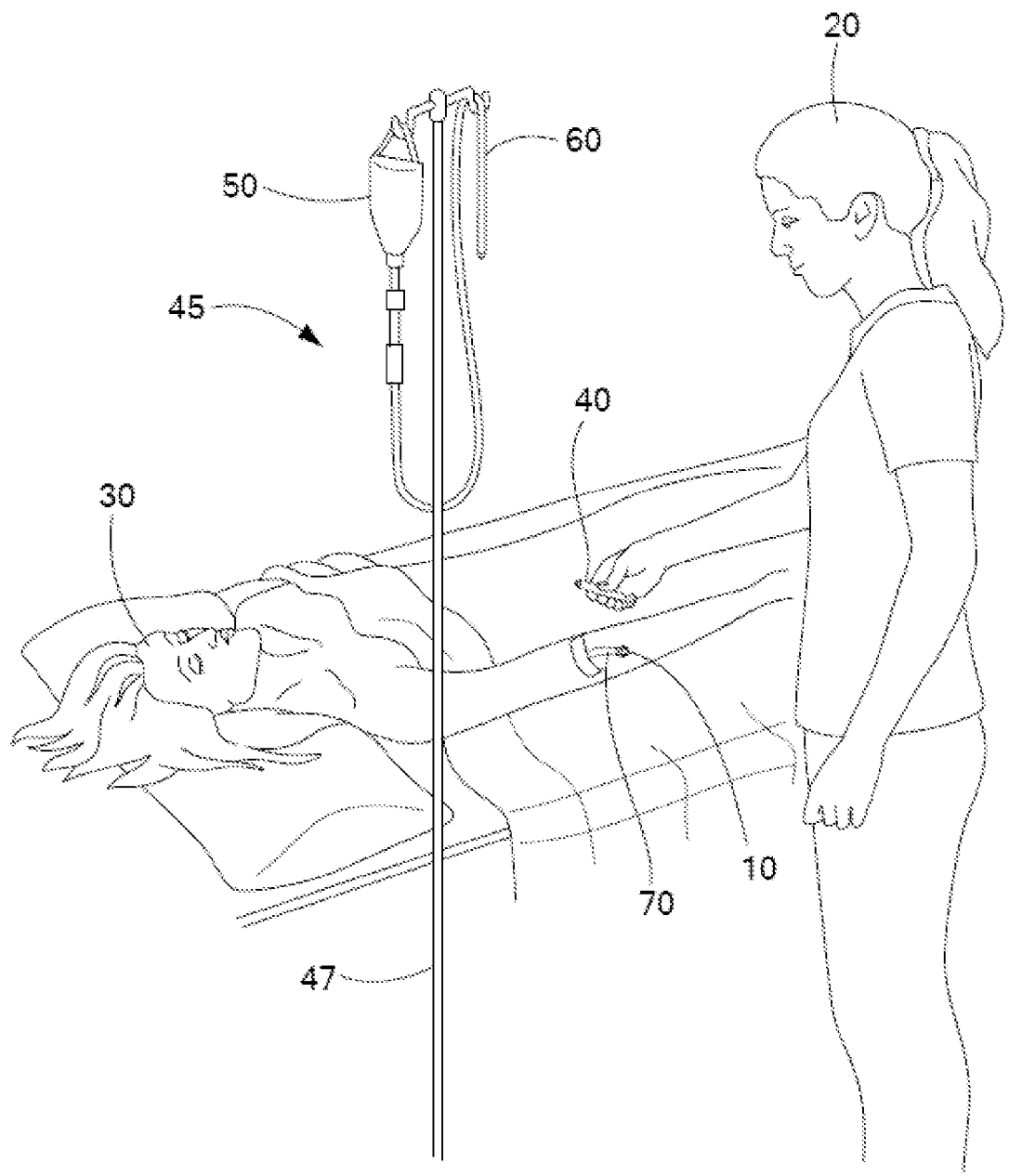
FIG. 1 schematically shows one use of a medical valve configured in accordance with one embodiment of the present invention.

FIG. 1 schematically shows one illustrative use of a medical valve 10 configured in accordance with illustrative embodiments of the invention. In this example, a catheter 70 connects the valve 10 with a patient's vein (the patient is identified by reference number 30). Adhesive tape or similar material may be coupled with the catheter 70 and patient's arm to ensure that the valve remains in place.

After the valve 10 is in place, a nurse, doctor, technician, practitioner, or other user (schematically identified by reference number 20) may intravenously deliver medication to the patient 30, who is lying in a hospital bed. To that end, after the valve is properly primed and flushed (e.g., with a saline flush), the nurse 20 swabs the top surface of the valve 10 to remove contaminants. Next, the nurse 20 uses a medical instrument (e.g., a syringe having a distally located blunt, luer tip complying with ANSI/ISO standards) to inject medication into the patient 30 through the valve 10. For example, the medical practitioner 20 may use the valve 10 to inject drugs such as heparin, antibiotic, pain medication, other intravenous medication, or other fluid deemed medically appropriate. Alternatively, the nurse 20 (or other user) may withdraw blood from the patient 30 through the valve 10.

The medical valve 10 may receive medication or other fluids from other means, such as through a gravity feed system 45. In general, traditional gravity feeding systems 45 often have a bag 50 (or bottle) containing a fluid (e.g., anesthesia medication) to be introduced into the patient 30. The bag 50 (or bottle) typically hangs from a pole 47 to allow for gravity feeding. The medical practitioner 20 then connects the bag/bottle 50 to the medical valve 10 using tubing 60 having an attached blunt tip. In illustrative embodiments, the blunt tip of the tubing has a luer taper that complies with the ANSI/ISO standard. After the tubing 60 is connected to the medical valve 10, gravity (or a pump) causes the fluid to begin flowing into the patient 30. In some embodiments, the feeding system 45 may include additional shut-off valves on the tubing 60 (e.g., stop-cock valves or clamps) to stop fluid flow without having to disconnect the tubing 60 from the valve 10. Accordingly, the valve 10 can be used in long-term "indwell" procedures.

After administering or withdrawing fluid from the patient 30, the nurse 20 should appropriately swab and flush the valve 10 and catheter 70 to remove contaminants and ensure proper operation. As known by those skilled in the art, there is a generally accepted valve swabbing and flushing protocol that should mitigate the likelihood of infection. Among other things, as summarized above, this protocol requires proper flushing and swabbing before and after the valve is used to deliver fluid to, or withdraw fluid from the patient.

Figure 2A:
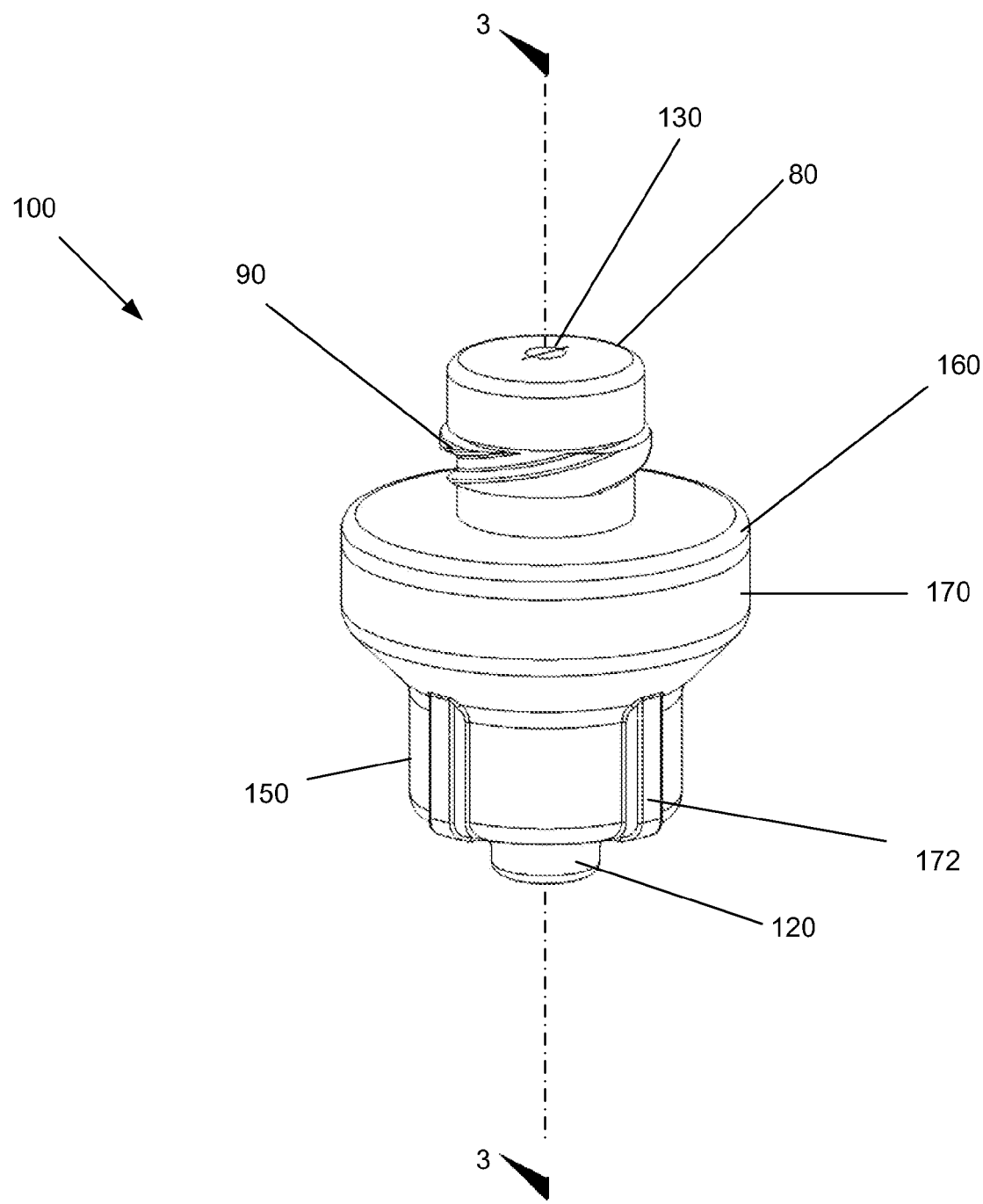
FIG. 2A schematically shows a perspective view of a medical valve configured in accordance with illustrative embodiments of the present invention.
Figure 2B:
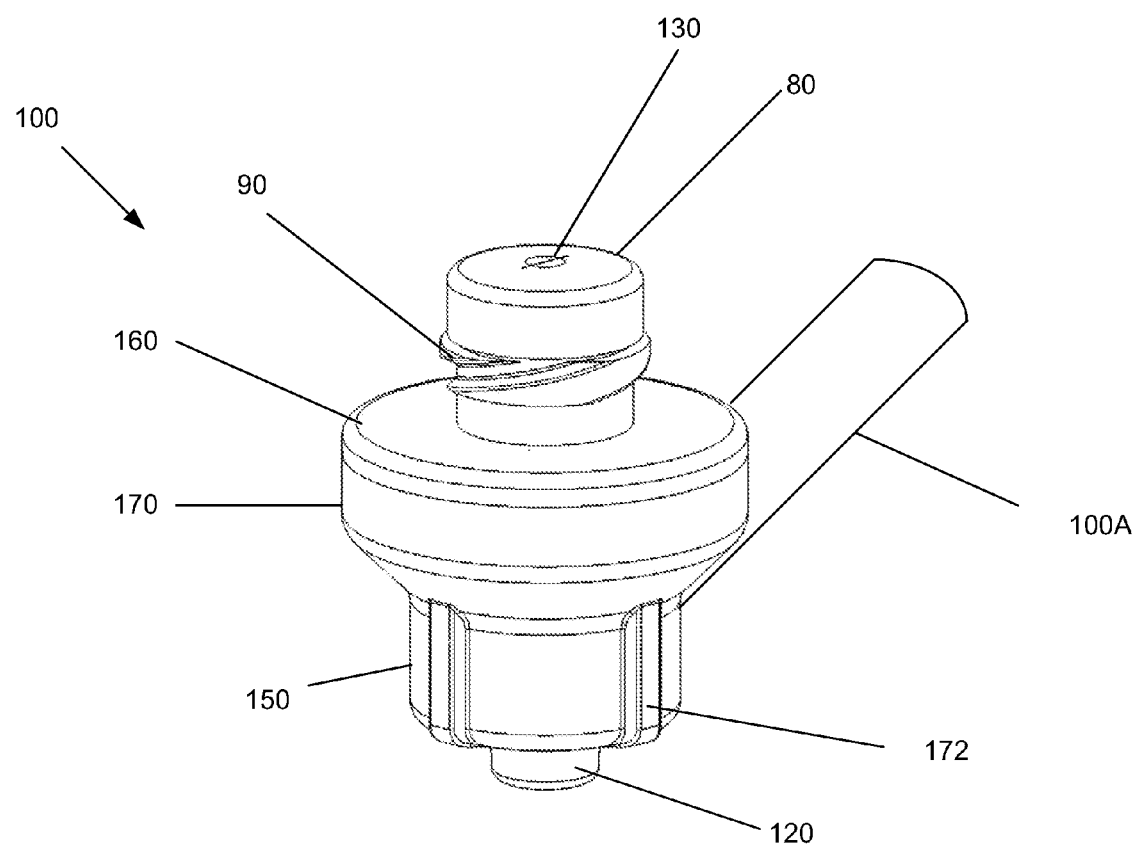
FIG. 2B schematically shows a perspective view of a medical valve of FIG. 2A with a Y-site branch.

FIG. 2A schematically shows a perspective view of the medical valve 10 shown in FIG. 1, while FIG. 2B schematically shows the same valve with a Y-site branch (discussed below). In illustrative embodiments, during withdrawal of the instrument, the valve 10 may be configured to have a substantially positive fluid displacement or a substantially neutral fluid displacement (between about plus or minus 1 microliter of fluid displacement, discussed below). In other words, withdrawal of a medical instrument 40 causes either a positive fluid displacement or essentially no or negligible fluid displacement at the distal end of the valve 10.

In this context, fluid displacement generally refers to the flow of fluid through the distal port 120 of the valve 10 (discussed below). Accordingly, a positive fluid displacement generally refers to fluid flowing in a distal direction through the distal port 120, while a negative fluid displacement generally refers to a fluid flowing in a proximal direction through the distal port 120. Of course, not all embodiments exhibit this quality. For example, in alternative embodiments, the valve 10 may have a negative fluid displacement when the instrument 40 is withdrawn.

It should be noted that the fluid displacements discussed herein refer to the "net" fluid displaced through the distal port 120. Specifically, during insertion or withdrawal of the instrument 40, the actual flow of fluid through the distal port 120 may change direction and thus, fluctuate. However, when considering this fluctuation, the net change in fluid flow through the distal port 120 should be 1) positive when the valve exhibits a "positive fluid displacement," and 2) negative when the valve exhibits a "negative fluid displacement." In a similar manner, a substantially neutral fluid displacement occurs when, as noted above, the valve 10 has a net fluid displacement of about plus or minus one microliter. Of course, the fluid displacement of the valve 10 is discussed herein in terms of one stroke of the instrument 40 (i.e., insertion or withdrawal of the instrument 40).

Ideally, a valve with a neutral displacement has 0.0 microliters of positive or negative fluid displacement. As suggested above, however, in practice, a neutral displacement actually can have a very slight positive or negative displacement (e.g., caused by a manufacturing tolerance), such as a displacement on the order of positive or negative one microliter, or less. In other words, in such embodiments, the volumes of fluid forced through the distal port 120 in a neutral displacement valve are negligible (ideally zero microliters) and should have a negligible impact on the goals of the valve.

Some embodiments may have a very low negative fluid displacement upon withdrawal. For example, such valves may have a negative fluid displacement of about one to two microliters (i.e., about one to two microliters of fluid drawback, which is proximally directed), or about one to two microliters positive fluid displacement (i.e., about one to two microliters of positively pushed fluid, which is distally directed). Although such amounts are in the positive or negative fluid displacement ranges, they still should represent a significant improvement over valves that exhibit higher positive or negative fluid displacements upon withdrawal.

The neutral, positive, or negative fluid displacement of a valve may be corrupted by manual handling of the valve 10, catheter 70 or the instrument 40 during the fluid transfer. For example, a slight inward force applied to the shaft of the medical instrument 40 (e.g., by the nurse's hand when simply holding the medical instrument 40) can have the effect of adding a positive fluid displacement from the medical instrument (when the force is applied) and, ultimately, through the valve 10. In fact, releasing this force from the medical instrument 40 actually may draw fluid proximally, causing a negative fluid displacement that further corrupts fluid displacement. These effects, however, should not be considered when determining the nature of fluid displacement through the distal port 120. To overcome the problem noted above with regard to squeezing the medical instrument shaft, for example, the nurse 20 can hold another part of the medical instrument that does not contain the fluid (e.g., stubs at the proximal end of the medical instrument 40).

To accomplish these desired goals, the valve 10 has a housing 100 forming an interior having a proximal port 110 for receiving the instrument 40, and the noted distal port 120 having the discussed fluid displacement properties. The valve 10 has an open mode that permits fluid flow through the valve 10, and a closed mode that prevents fluid flow through the valve 10. To that end, the interior contains a valve mechanism that selectively controls (i.e., allow/permits) fluid flow through the valve 10. The fluid passes through a complete fluid path that extends between the proximal port 110 and the distal port 120.

It should be noted that although much of the discussion herein refers to the proximal port 110 as an inlet, and the distal port 120 as an outlet, the proximal and distal ports 110 and 120 also may be respectively used as outlet and inlet ports. Discussion of these ports in either configuration therefore is for illustrative purposes only.

The valve 10 is considered to provide a low pressure seal at its proximal end 110. To that end, the proximal end 110 of the medical valve 10 has a resilient proximal gland 80 with a resealable aperture 130 that extends entirely through its profile. The aperture 130 may, for example, be a pierced hole or a slit. Alternatively, the proximal gland 80 may be molded with the aperture 130. In some embodiments, when the valve 10 is in the closed mode (see FIG. 9A) the aperture 130 may be held closed by the inner surface of the housing 100. In that case, the inner diameter of the proximal port 110 is smaller than the outer diameter of the proximal gland 80 and thus, the proximal port 110 squeezes the aperture 130 closed. Alternatively, as shown in FIG. 2A, the resilient member may be formed so that the aperture 130 normally stays closed in the absence of radially inward force provided by the inner diameter of the proximal port 110. In other words, the proximal gland 80 is formed so that the aperture 130 normally is closed.

Figure 9A:
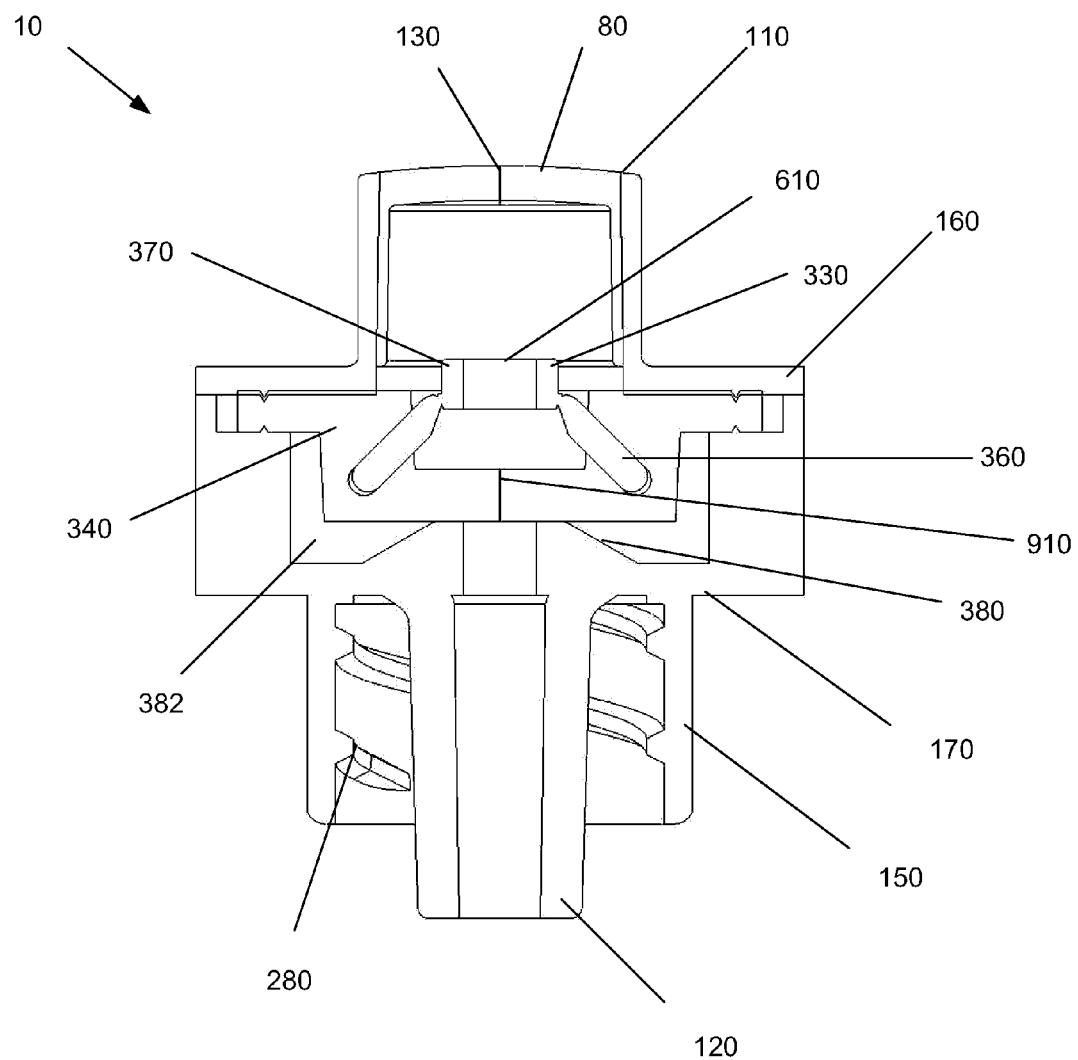
FIG. 9A schematically shows a cross-sectional view of an alternative embodiment having an actuator with two leg members. This figure shows the valve in the closed mode.

As suggested above, the proximal gland 80 may be flush with or extend slightly above the exterior inlet face 140 of the inlet housing 160 (see FIG. 9A). The proximal gland 80 and the exterior inlet face 140 thus present a swabbable surface, i.e., it may be easily wiped clean with an alcohol swab, for example, or other swab. Alternatively, the proximal gland 80 can be molded over the proximal port 110 (see FIG. 2A), to provide the swabbable surface. Such valves typically have been referred to in the art as "swabbable valves." Various other embodiments, however, may relate to other types of valves and thus, not all embodiments are limited to swabbable valves. In addition, some embodiments may be used with instruments 40 having blunt tips that do not comply with the ANSI/ISO luer standard.

The outside surface of the valve proximal port 110 may also have inlet threads 90 for connecting the medical instrument 40. Alternatively or in addition, the proximal end may have a slip design for accepting instruments 40 that do not have a threaded interconnect. In a similar manner, the distal end of the valve 10 has a skirt 150 containing threads 280 (see FIG. 3) for connecting a threaded port of the catheter of FIG. 1, or a different medical instrument, to the valve distal port 120. The skirt 150 may also include ribs 172 that allow the medical practitioner 20 to easily grasp and handle the valve 10. The proximal end inlet threads 90 and the distal end threads 280 preferably comply with ANSI/ISO standards (e.g., they are able to receive/connect to medical instruments complying with ANSI/ISO standards). In addition to the threads described above, the internal geometry of the inlet housing 160 (e.g., shown in FIG. 3, discussed below) may taper in an opposite direction to that of a standard luer taper.

Figure 3:
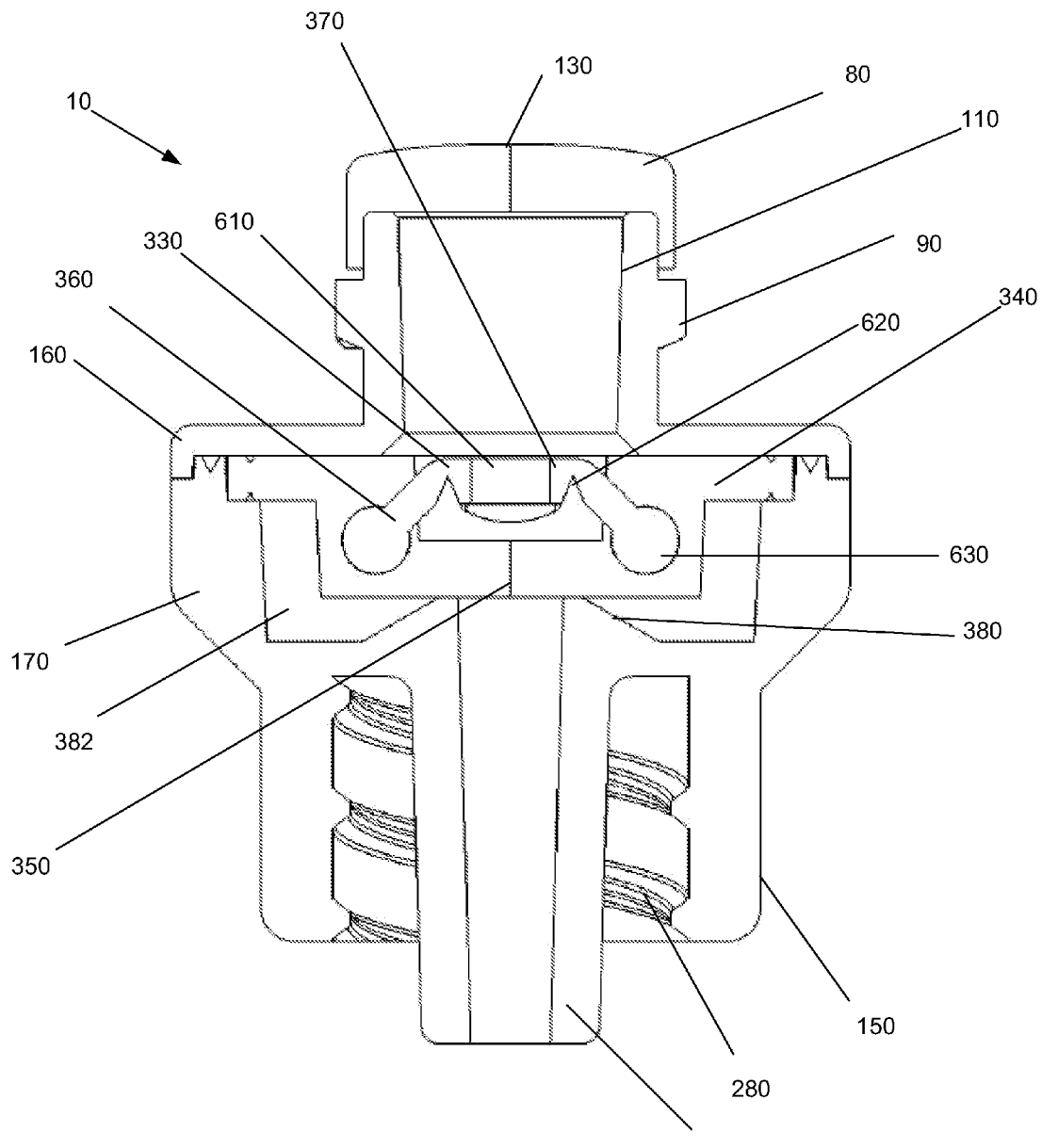
FIG. 3 schematically shows a cross-sectional view of the valve shown in FIG. 2A in the closed mode along line 3-3.

FIG. 3 schematically shows the cross section of the valve shown in FIG. 2A along the line 3-3. In this embodiment, the proximal seal 80 is molded over the proximal port 110. However, other embodiments may have the proximal seal 80 configuration shown in FIG. 9A. FIG. 3 shows the valve 10 in the closed position when no medical instrument or other instrument is inserted through the proximal port 110. As shown, the housing 100 includes an inlet housing 160 and an outlet housing 170, which connect together to form the interior of the medical valve 10. Within the interior, the medical valve 10 has a valve mechanism. The inlet housing 160 and the outlet housing 170 may be joined together in a variety of ways, including a snap-fit connection, ultrasonic welding, plastic welding, or other method conventionally used in the art.

The internal valve mechanism includes an actuator 330 that cooperates with a resilient member 340 to selectively open and close the valve 10. In the embodiment shown in FIG. 3, the actuator 330 is typically formed from a relatively rigid material (e.g., plastic). In contrast, the resilient member 340 is typically formed from a resilient material that allows it to easily deform (e.g., silicone). Details of the interaction between the actuator 330 and the resilient member 340 are discussed in greater detail below, with respect to FIG. 5.

As shown in FIG. 3, the actuator 330 may have leg members 360 extending out from a body portion 370. As discussed in greater detail below, the leg members 360 apply a force to the resilient member 340 as the actuator 330 moves distally (e.g., when a medical implement is inserted into the valve 10). The force applied to the resilient member 340 causes the resilient member 340 to deform causing an aperture 350 through the resilient member 340 to open. Once the aperture 350 is open, the valve 10 is considered to be in the open mode.

To aid in the transition from the open mode and the closed mode, the valve 10 can also include a valve seat 380 located distally from the resilient member 340. The resilient member 340 can seal against the valve seat to prevent leakage past the valve seat 380 and resilient member 340 and into space 382. In some embodiments, the valve seat 380 can be angled (as shown in FIG. 3). As discussed in greater detail below, the angled valve seat 380 aids in valve 10 and aperture 350 opening because the resilient member 340 can deform to the shape of the valve seat 380 as the actuator 330 moves distally.

Figure 4:
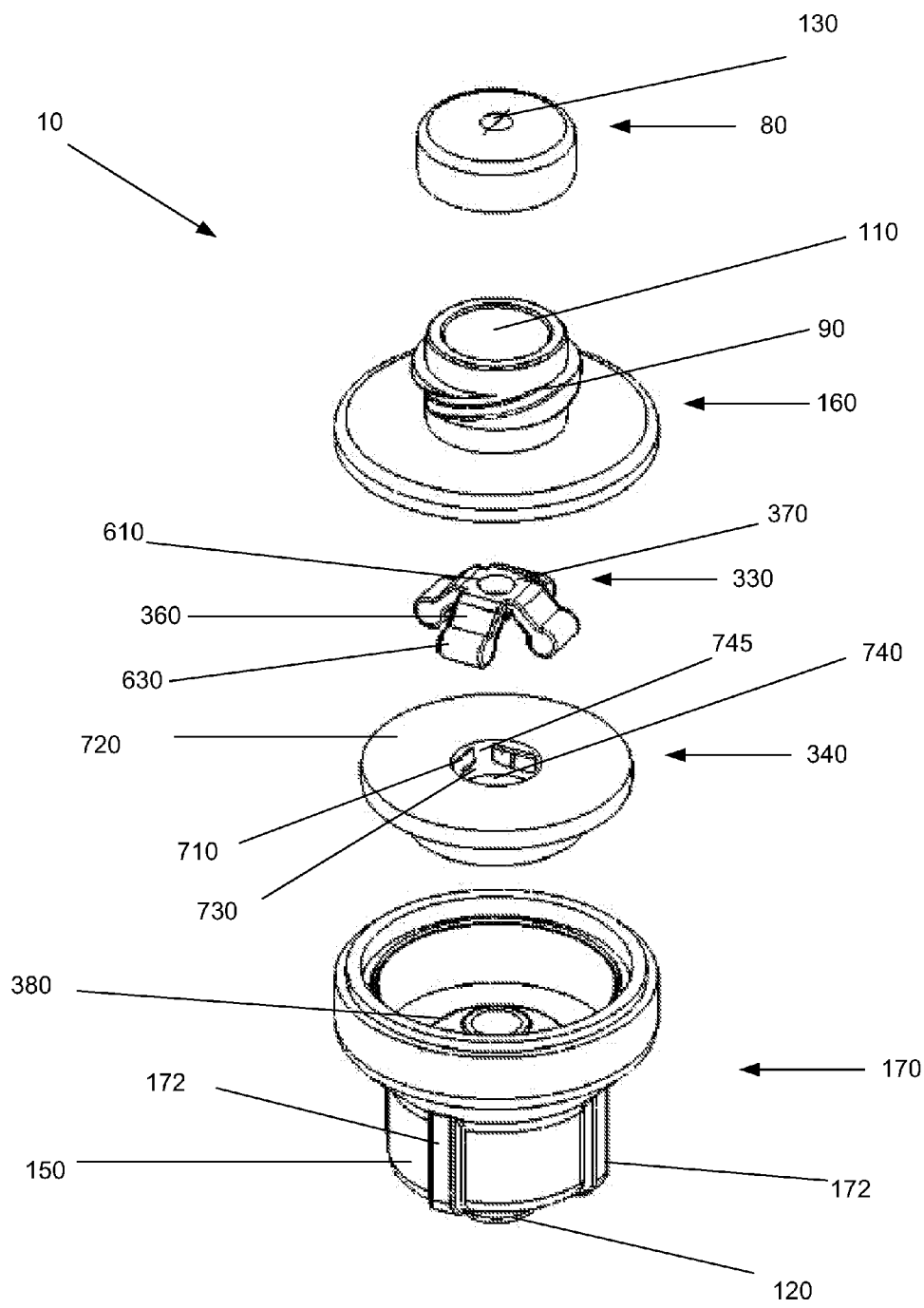
FIG. 4 schematically shows a perspective exploded view of the medical valve shown in FIG. 2A.

FIG. 4 schematically shows an exploded perspective view of the medical valve 10 shown in FIG. 3. Although FIG. 4 shows five pieces that may be assembled to form the valve 10 (i.e., the proximal gland 80, the inlet housing 160, the actuator 330, the resilient member 340, and the outlet housing 170), alternative manufacturing processes can be used to reduce the total number of components. For example, the proximal gland 80 and the inlet housing 160 can be manufactured in a "two-shot" or "over-mold" process. As known by those in the art, the two-shot manufacturing process creates one piece formed with two materials (i.e., the elastomeric proximal gland 80 material and the material forming the rigid inlet housing 160) that are chemically bonded to one another. In a similar manner, the resilient member 340 and the outlet housing 170 can be manufactured in a two-shot process to form a one-piece bottom housing. Alternatively, the actuator 330 and the resilient member 340 can be manufactured in a two-shot process to form a single internal valve mechanism. Therefore, the "two-shot" manufacturing process can reduce the total number of valve components to as few as three, significantly reducing assembly complexity. In addition, use of a two-shot process can significantly minimize the possibility of fluid leaking between the proximal gland 80 and inlet housing 160. In a similar manner, use of a two shot process can significantly minimize the possibility of fluid leaking between the resilient member 340 and the outlet housing 170, or the resilient member 340 and the actuator 330.

As mentioned above and as illustrated in FIG. 5, distal movement of the actuator 330 opens the valve 10. In particular, when a medical practitioner inserts a medical instrument 40 into the valve 10 and the actuator 330 begins to move distally, the resilient member 340 will begin to deform into space 382. Specifically, in this embodiment, the actuator 330 radially expands the resilient member 340 to open the valve 10. As the resilient member 340 deforms, the aperture 350 through the resilient member 340 opens, fluidly communicating the proximal port 110 and the distal port 120. The nurse or medical practitioner 20 can then transfer fluid to or from the patient 30.

Figure 6:
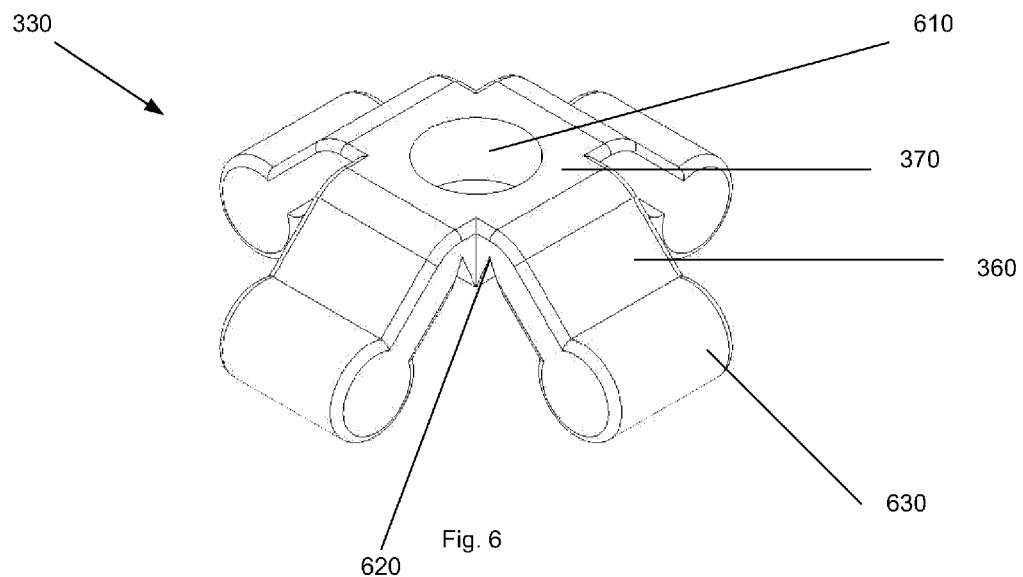
FIG. 6 schematically shows a perspective view of an illustrative embodiment of an actuator within the valve of FIG. 2A.
Figure 7:
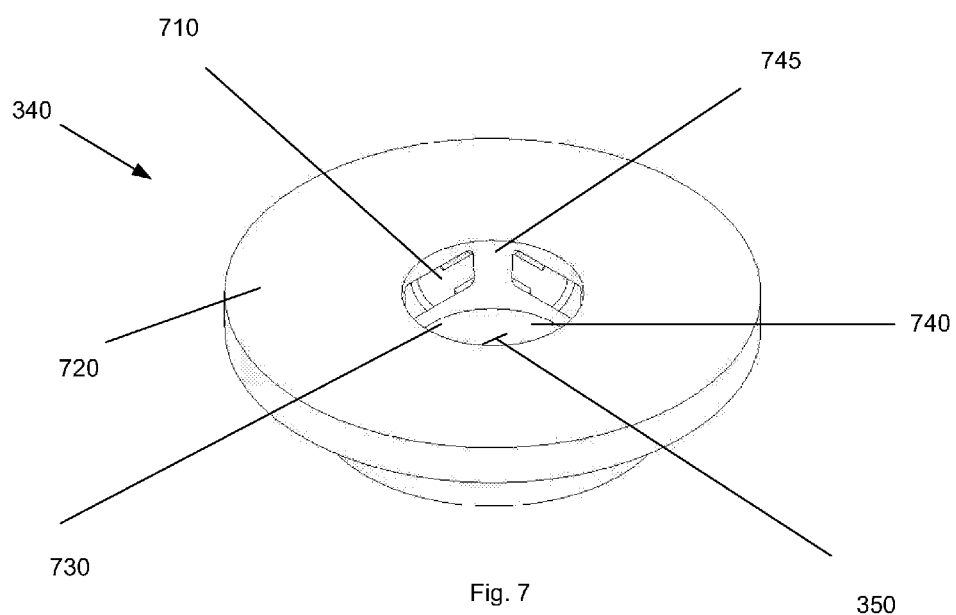
FIG. 7 schematically shows a perspective view of an illustrative embodiment of a resilient member within the valve of FIG. 2A.

FIGS. 6 and 7 schematically show perspective views of the actuator 330 and resilient member 340, respectively. Specifically, FIG. 6 schematically shows additional details of the actuator 330, which, as noted above, has a body portion 370 and a plurality of leg members 360 extending from the body portion 370. In some embodiments, the leg members 360 can be connected to the body portion 370 using hinges 620 that allow the leg members 360 to flex and/or move with respect to the body portion 370. In particular, the leg members 360 can pivot about the body portion 370 and flex/move radially outwardly as the actuator 330 moves distally. This flexing and pivoting by the leg members 360 applies a radially outward force against the resilient member 340 and causes the aperture 350 to open.

In some embodiments, the leg members 360 can include enlarged end portions 630 located near the bottom of the leg member 360. The enlarged end portions 630 can cooperate with leg recesses 710 (FIG. 7) within the resilient member 340 to provide a larger surface area for the application of the radial force on the aperture 350. The cooperation between the enlarged leg portions 630 and the leg recesses 710 also secures the actuator 330 within the valve 10 (e.g., prevents the actuator 330 from moving or spinning within the valve 10). Although four leg members 360 are shown in FIG. 6, any number of leg members 360 can be used in accordance with various embodiments of this invention. For example, and as discussed in greater detail below, the actuator 330 may only have two leg members 360.

As mentioned above, the hinge 620 allows the leg members 360 to flex/move and pivot with respect to the body portion 370. The hinge can be any number of elements that allow such flexion/movement and pivoting. For example, as shown in FIG. 6, the hinge 620 may simply be a thinned area between each of the leg members 360 and the body portion 370 (e.g., a living hinge). Alternatively, the hinge 620 can be a separate and distinct element that connects the leg member 360 to the body portion 370. For example, the hinge 620 may be an elastomeric sleeve or elastomeric portion located between each leg member 360 and the body portion 370.

In some embodiments, the actuator 330 has an actuator channel 610 passing through the body portion 370. When the valve 10 is in the open mode, the actuator channel 610 may be part of the fluid channel through the valve. Although FIG. 6 shows an actuator channel 610 with a circular opening, any shape or size opening that allows appropriate fluid flow through the actuator 330 can be used.

FIG. 7 schematically shows more details of the resilient member 340 shown in the previous figures. As shown in FIG. 7, the resilient member has a proximal surface 720 and an aperture surface 740. The aperture surface 740 may be recessed from the proximal surface 720 to create an actuator recess 730 having a vertical wall 745 between the proximal surface 720 and the aperture surface 740. In preferred embodiments, and as discussed briefly above, the resilient member 340 may have leg recesses 710 located on the vertical wall 745 between the aperture surface 740 and the proximal surface 720. The leg recesses 710 are sized appropriately to receive the leg members 360, and in particular, the leg ends 630, and form a fluid tight seal between the actuator 330 and the resilient member 340. As best shown in FIG. 3, the actuator 330 can sit within the resilient member recess 730, such that the leg ends 630 are within the leg recesses 710 and the top surface of the body portion 370 is substantially flush with the proximal surface 720.

As mentioned above, the resilient member has an aperture 350 that opens as the actuator moves distally. In preferred embodiments, the aperture 350 is located on and passes through the aperture surface 740. Although the aperture 350 can be any number of elements that allow fluid to pass through the valve when the valve is in the open mode (e.g., a slit, a pinhole, a cut-out, etc.), in preferred embodiments, the aperture 350 is a slit, similar to the slit 130 passing through the proximal gland 80. The slit can be self-sealing such that it automatically closes and seals when the valve 10 is in the closed mode. In other words, no additional elements or interactions are required to close and seal the slit.

When the valve 10 is in the open mode, the resilient member 340 may provide a force against the actuator 330 that biases the actuator 330 proximally. Therefore, as the medical practitioner 20 begins to remove the medical instrument 40 (e.g., as the medical practitioner 20 moves the medical instrument 40 proximally), the proximal bias provided by the resilient member 340 will begin to force the actuator 330 proximally. As the actuator 330 moves proximally, the leg members 360 will begin to flex inward towards their at rest position, and the radial force on the resilient member 340 and aperture 350 will decrease. As the radial force decreases, the aperture 350 will continue to close until the aperture 350 and the valve 10 are fully closed.

As mentioned above, some embodiments can exhibit a positive or substantially neutral displacement upon withdrawal of the instrument 40. For example, as the medical practitioner 20 inserts the medical instrument 40, the volume around the actuator 330 and the resilient member 340 expands as the resilient member 340 stretches and deforms. When the instrument 40 is removed, this volume collapses and forces the fluid above the resilient member 340 to move distally, thereby creating a positive displacement at the distal port 120. In order to achieve a substantially neutral displacement, the amount that the resilient member 340 stretches and/or the length of the leg members 360 may be adjusted (e.g., adjusting the amount the actuator 330 deforms the resilient member 340). In other words, as the amount that the resilient member stretches and/or the length of the leg members decrease, the amount of fluid displacement will also decrease because the change in volume around the actuator 330 and resilient member 340 will decrease. Therefore, when the leg member length is sufficiently short and/or the amount of resilient member 340 stretching is sufficiently small, there will be only a minimal volume change around the actuator 330 and resilient member 340, and a substantially neutral displacement at the distal port 120.

Figure 8:
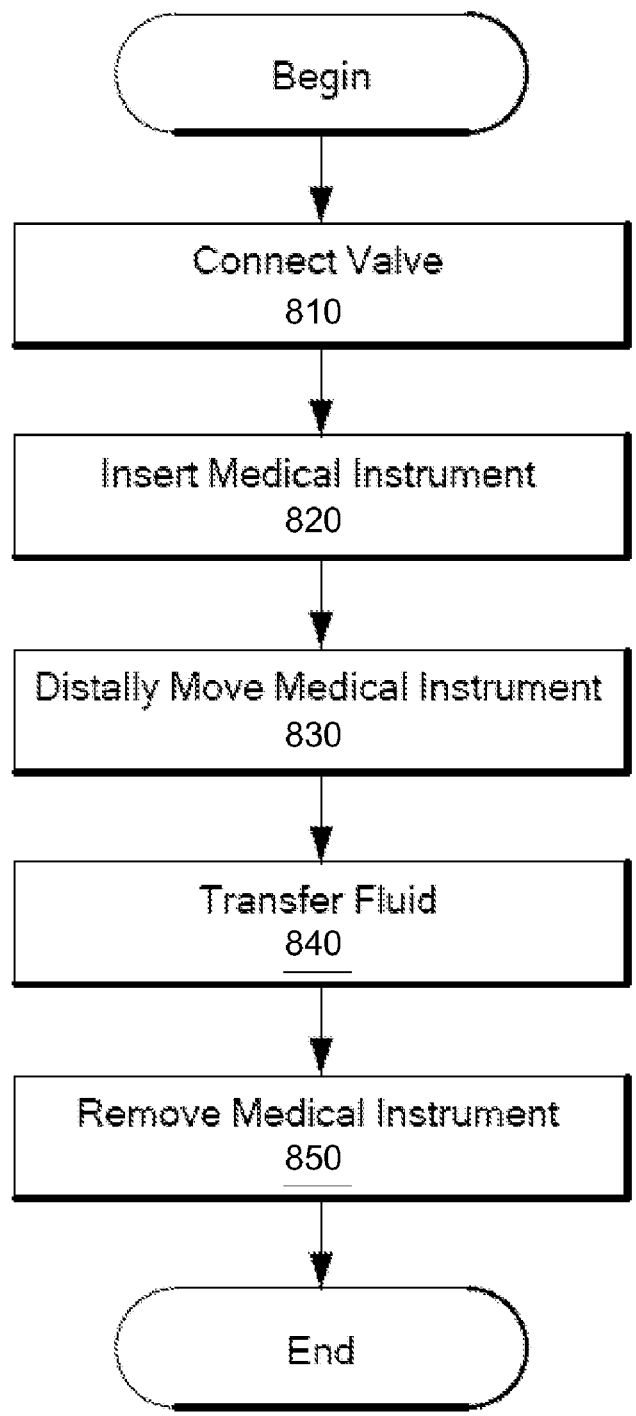
FIG. 8 shows a process of using the medical valve shown in FIG. 2A in accordance with illustrative embodiments of the invention.

FIG. 8 shows a process illustrating one of a plurality of illustrative uses of the medical valve 10. It is important to reiterate that, according to good medical practice, the proximal port 110 and distal port 120 of medical valve 10 should be cleaned (e.g., swabbed) prior to any connection and after any disconnection. After properly swabbing the distal port 120 of the medical valve 10, a medical practitioner 20 connects the medical valve 10 to the patient 30 (step 810). To do so, the medical practitioner 20 may connect the distal port 120 of the medical valve 10 to the catheter 70, which terminates at a needle inserted into the patient 30 (see FIG. 1).

After connecting the valve 10 to the patient 30, the medical practitioner 20 swabs the valve proximal port 110 and inserts the medical instrument 40 into the proximal port 110 (step 820). As the medical practitioner 20 moves the medical instrument distally (step 830) into the medical valve 10, the tip of the instrument 40 contacts the proximal surface of the actuator 330 and begins to move the actuator 330 distally within the valve 10. As the actuator 330 continues to move distally, the leg members 360 begin to flex and pivot about the body portion 370 and begin to apply a radially outward force to the resilient member 340 and aperture 350. As the actuator 330 and leg members 360 move and flex further, the aperture 350 opens providing fluid communication between the proximal port 110 and the distal port 120. At this point, the valve 10 is open.

Figure 5:
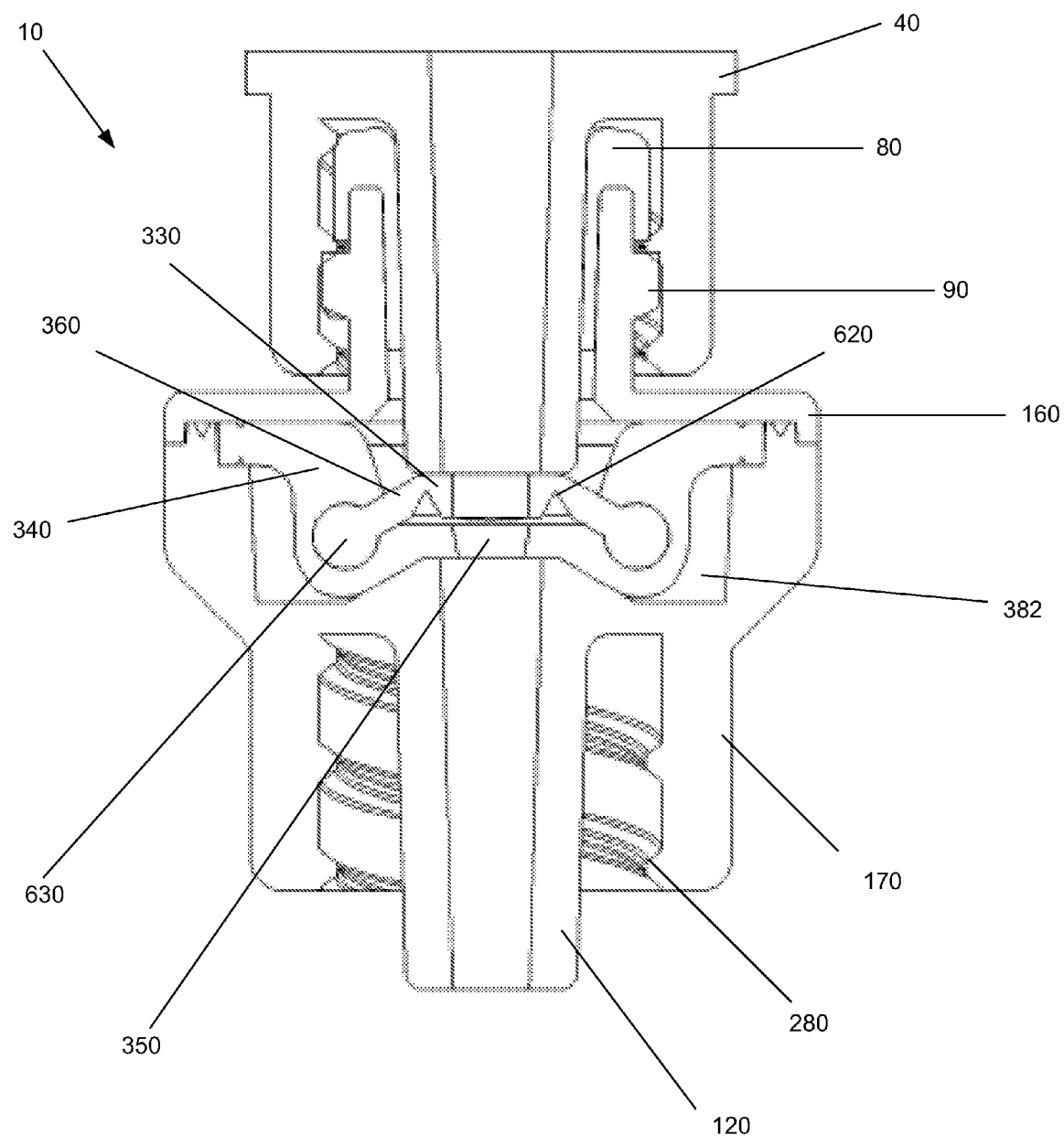
FIG. 5 schematically shows a cross-sectional view of the valve shown in FIG. 2A in the open mode along line 3-3.

It is important to note that the valve 10 requires a relatively low prime volume because the medical instrument 40 used to open the medical valve 10 takes up much of the volume within the medical valve 10 (see FIG. 5). Additionally, because the disconnect and valve closing time may be short, a vacuum may be formed in the void volume when the medical instrument 40 is disconnected.

After opening the valve 10, the medical practitioner 20 can transfer fluids to or from the patient (step 840). For example, if the medical practitioner 20 wishes to administer a medication to the patient 30, he/she may depress the medical instrument plunger 40 (e.g., for a syringe) and transfer the medication into the patient 30. Alternatively, the medical practitioner 20 may withdraw blood from the patient 30.

After completing the fluid transfer(s), the medical practitioner 20 can remove the medical instrument (step 850). As discussed above, the medical practitioner 20 should take care not to squeeze the sides of the medical instrument 40. Doing so may create a false positive or negative displacement at the distal port 120 of the medical valve 10. If done properly, removal of the medical instrument 40 may result in a substantially neutral or positive displacement at the valve distal port 120.

As discussed above with reference to FIGS. 3 and 5, the actuator 330 will begin to move proximally as the medical practitioner 30 withdraws the medical instrument 40 from the medical valve 10. As the actuator moves proximally towards the at rest position, the radially outward force applied to the resilient member and aperture will decrease, allowing the resilient member 340 to return to its at rest position, and closing the aperture 350.

It should be noted that the above embodiments describe a medical valve 10 in which the proximal port 110 and the distal port 120 are aligned with one another. However, in various other embodiments of the present invention, the medical valve 10 can include a Y-site branch 100A (e.g., see FIG. 2B). The Y-site branch 100A may extend from the housing 100 to form a Y-site channel. The Y-site channel may be in fluid communication with the valve distal port 120. To ensure sterility, the Y-site channel may have a resilient diaphragm, or a valve of some type. Alternatively, the Y-site channel may have no valving means.

Figure 9B:
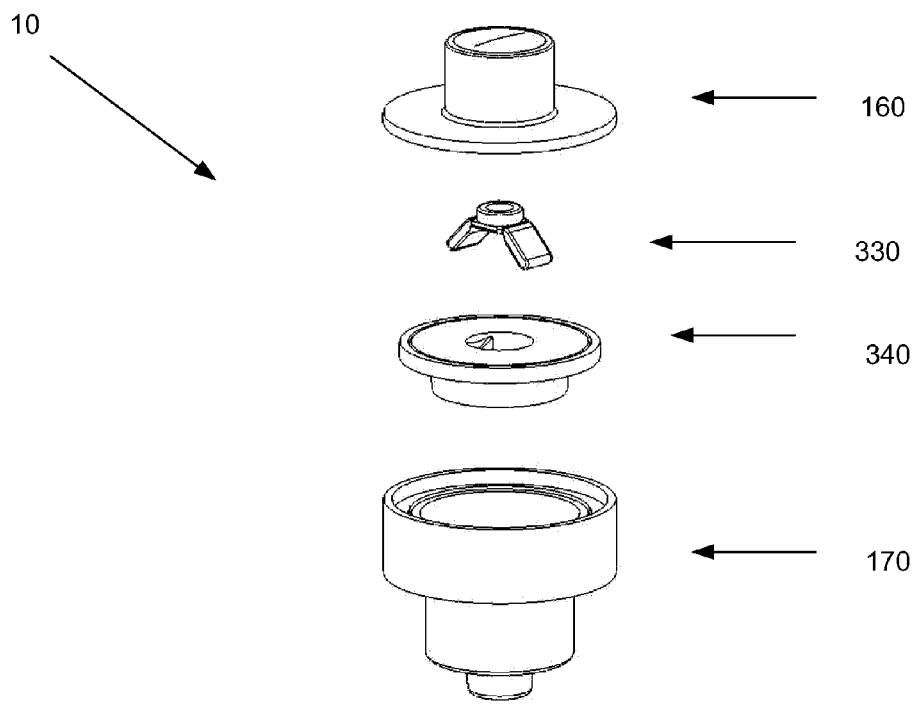
FIG. 9B schematically shows a perspective exploded view of the medical valve shown in FIG. 9A.
Figure 9C:
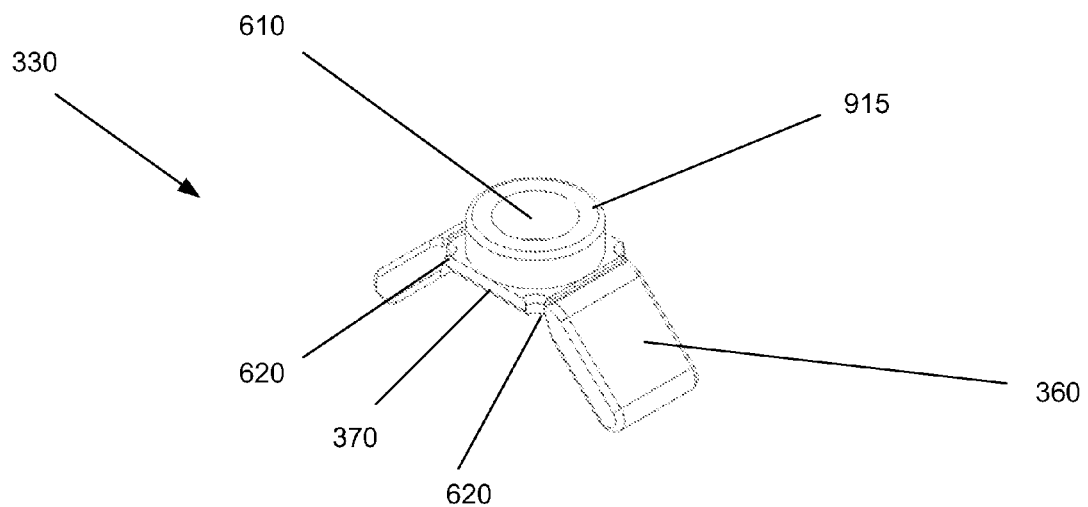
FIG. 9C schematically shows an illustrative embodiment of the actuator within the valve of FIG. 9A.

As mentioned above, some embodiments of the present invention can have a different number of leg members 360. For example, as shown in FIGS. 9A through 9C, some embodiments may have an actuator 330 with only two leg members 360. In such embodiments, the leg members 360 should be oriented such that they are located on either side of the aperture 350 in the resilient member 340 so that the force applied to the resilient member 340 by the leg members (e.g., during valve opening) opens the aperture 350 (as opposed to keeping the aperture 350 closed if positioned at the ends of the aperture 350). Additionally, as shown in FIG. 9A, the actuator 330 need not sit within resilient member recess 730. In fact, the majority of the body portion 370 can extend proximally from the proximal surface 720 of the resilient member 340.

As shown in FIGS. 9B and 9C, the valve components (inlet housing 160, outlet housing 170, resilient member 340, and actuator 330) are structurally very similar to the previous embodiment (except for the actuator 330 having only two leg members 360). To that end, this embodiment operates in a substantially similar manner as the embodiments described above and shown in FIGS. 3 and 5. However, it should be noted that the body portion 370 of the actuator 330 can have a raised contact surface 915. The medical instrument 40 contacts the raised contact surface 915 as the valve 10 opens and closes.

Figure 10A:
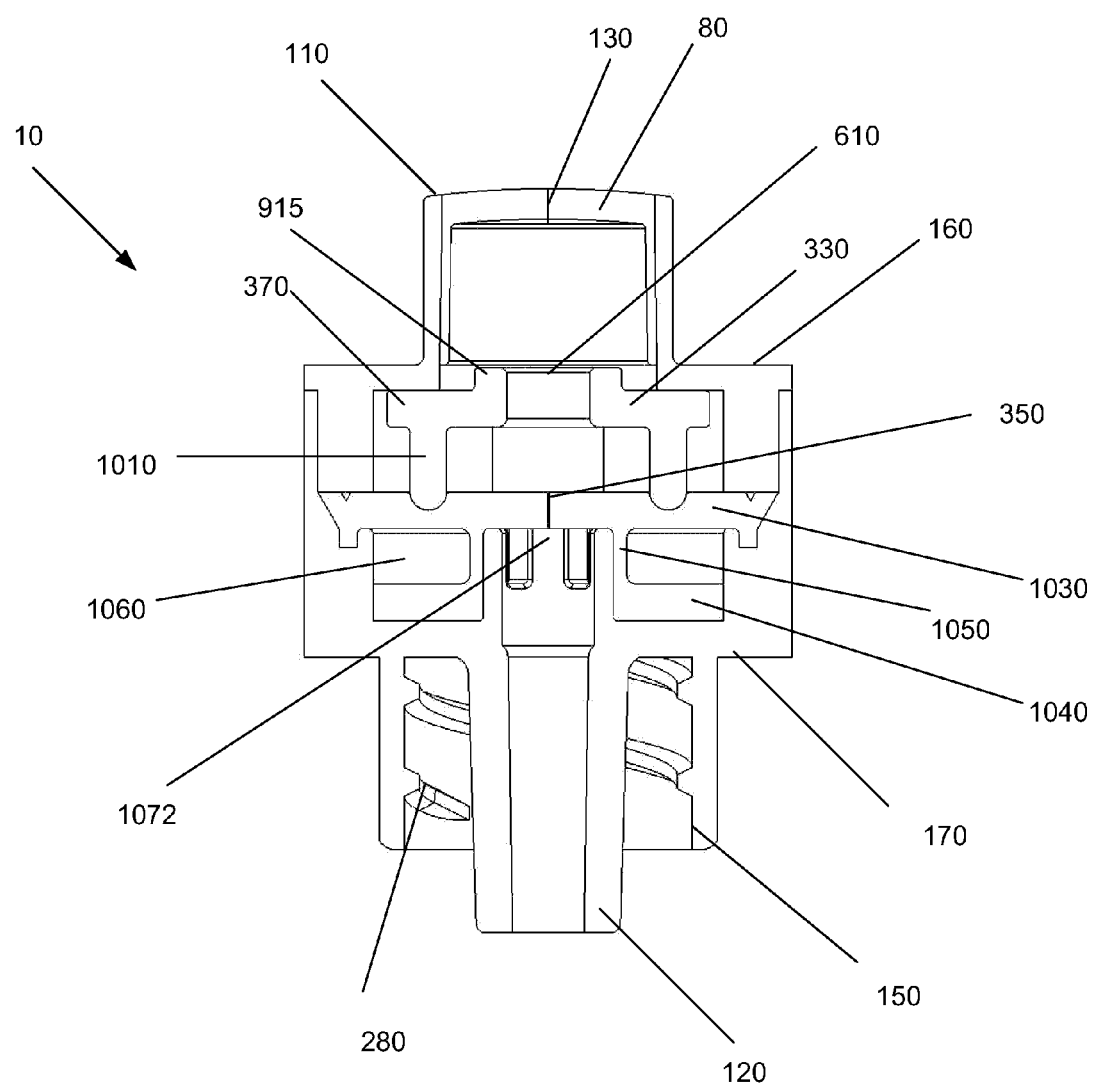
FIG. 10A schematically shows a cross-sectional view of another alternative embodiment having an outlet with proximally extending post members. This figure shows the valve in the closed mode.
Figure 10B:
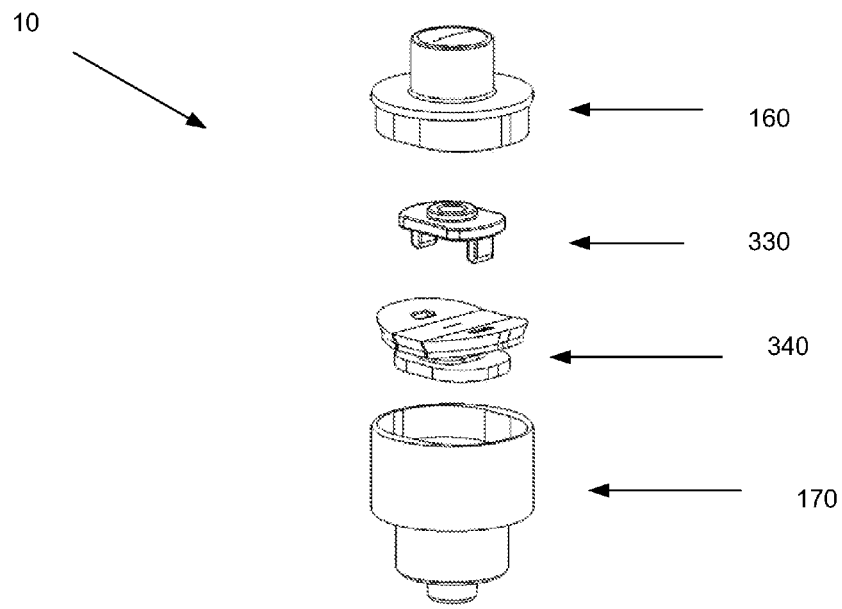
FIG. 10B schematically shows a perspective exploded view of the medical valve shown in FIG. 10A.
Figure 10C:
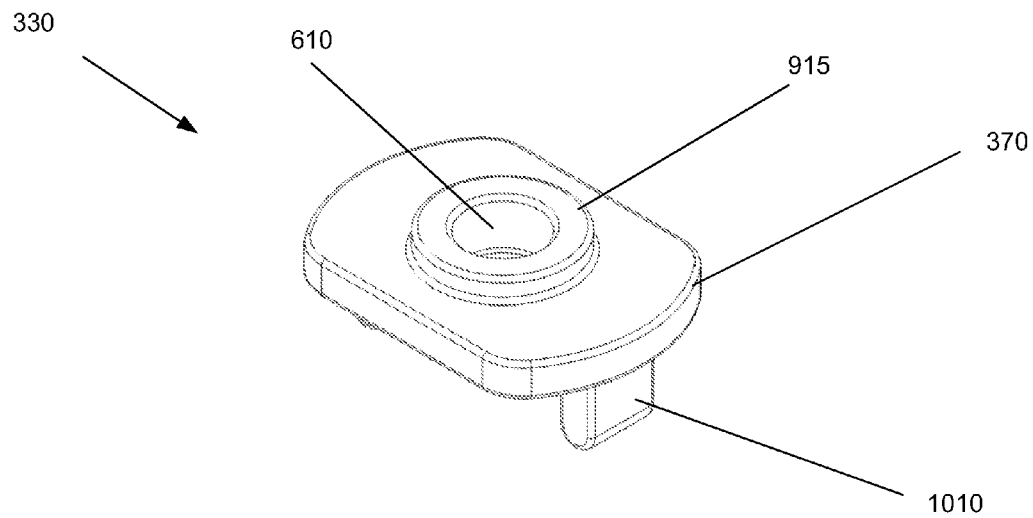
FIG. 10C schematically shows an illustrative embodiment of the actuator within the valve of FIG. 10A.

FIG. 10A schematically shows a front cross-sectional view of another embodiment of the medical valve 10. As mentioned above, and as shown in FIGS. 10A through 10C, the leg members 360 can be substantially stationary with respect to the body portion 370 (e.g., they are not connected by the hinge 620). Although the stationary leg members 1010 do not flex or move with respect to the body portion 370, they perform substantially the same function as the moveable leg members 360. Specifically, as the actuator 330 moves distally within the valve 10, the stationary leg members 1010 and the actuator 330 deform the resilient member 340 to open the aperture 350 and the valve 10. However, because the stationary leg members 1010 do not provide a radially outward force like the moveable leg members 360, the aperture 350 opens because of the deformation of the resilient member 340 over the protrusions 1070A-D (see FIG. 10F), which are described in more detail below.

Figure 10D:
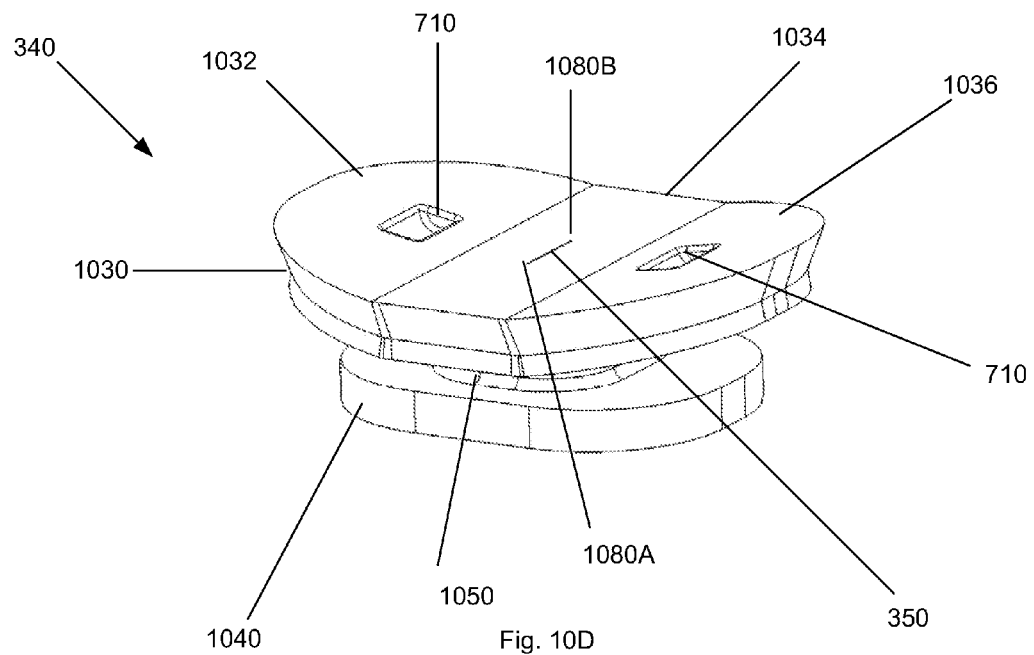
FIG. 10D schematically shows an illustrative embodiment of the resilient member within the valve of FIG. 10A. This figure shows the resilient member as molded.
Figure 10E:
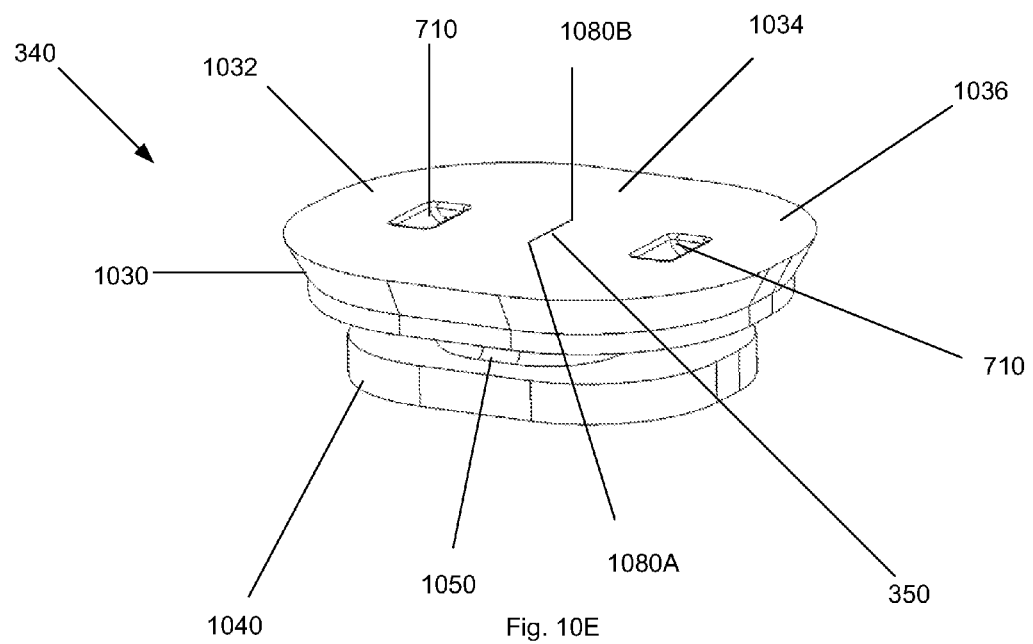
FIG. 10E schematically shows an illustrative embodiment of the resilient member within the valve of FIG. 10A. This figure shows the resilient member after assembly.

As shown in FIG. 10D and 10E, in some embodiments, the resilient member 340 can have a slightly different structure from the embodiments described above. In particular, the resilient member 340 can have a proximal portion 1030 and a distal portion 1040 connected by an intermediate portion 1050. The intermediate portion 1050 has a reduced diameter as compared to the proximal portion 1030 and distal portion 1040 so that a gap 1060 is created between the proximal portion 1030 and distal portion 1040 (FIG. 10A) when the valve 10 is assembled.

As shown in FIG. 10D, in the "as molded state", the proximal portion 1030 of the resilient member 340 can have three portions—an angled left portion 1032, a middle portion 1034, and an angled right portion 1036. However, when the valve is in its "as assembled state", the left portion 1032 and the right portion 1036 deform creating a substantially flat surface across the proximal portion 1030 (FIG. 10E). The deformation of the angled left portion 1032 and the angled right portion 1036 creates a compressive force on the sides of the aperture 350, helping to keep the aperture 350 closed when the valve 10 is in the closed mode. Additionally, unlike the embodiments described above, the leg recesses 710 and the aperture 350 are not located in a recess. Rather, the leg recesses 710 and the aperture 350 are located on the proximal surface 720.

Figure 10F:
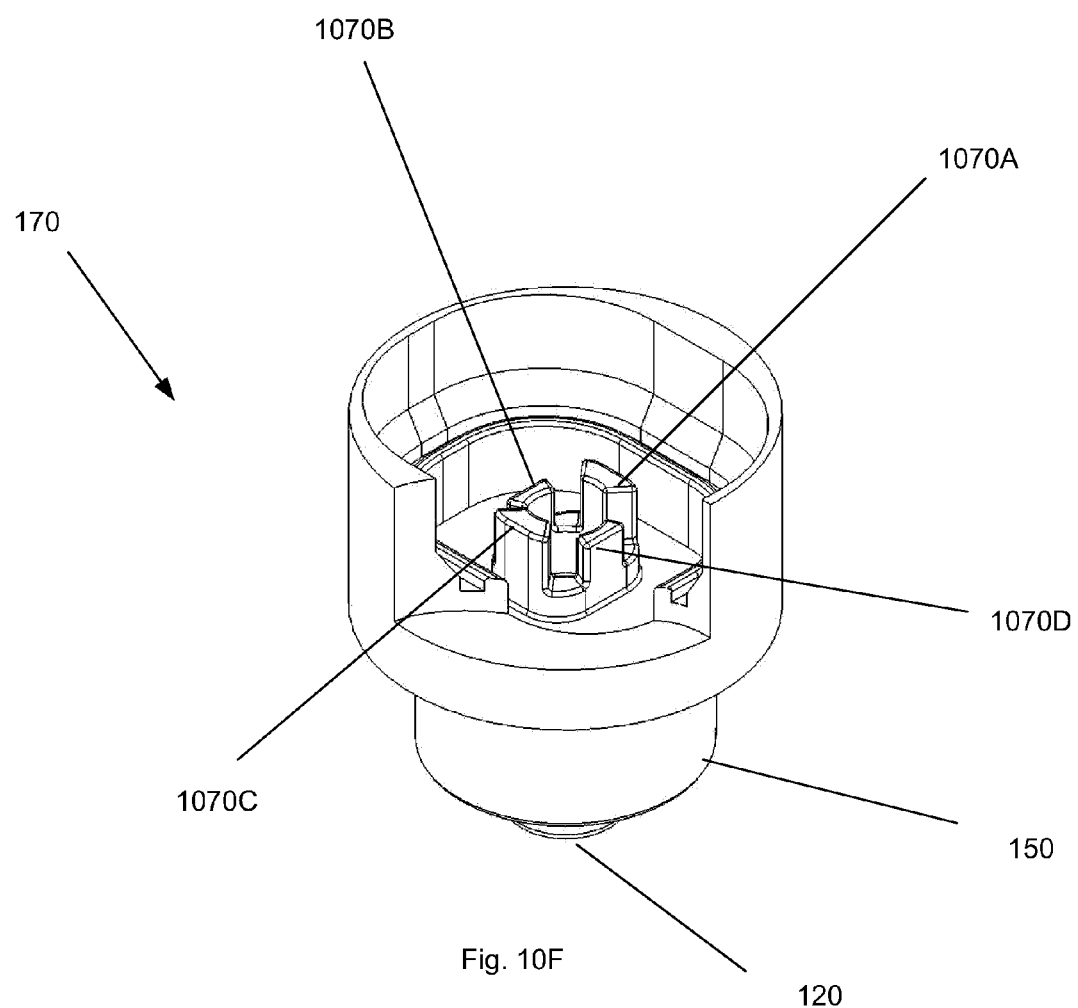
FIG. 10F schematically shows an illustrative embodiment of the outlet of the valve of FIG. 10A. This figure shows a section of the outlet cut-away to illustrate the proximally extending protrusion.

As shown in FIG. 10F, and as suggested above, the outlet 170 of this embodiment can include a number of protrusions 1070A, B, C, and D extending proximally from the outlet 170. In some embodiments, protrusions 1070A and 1070C can be taller than protrusions 1070B and 1070D. As discussed in greater detail below, the taller protrusions 1070A and 1070C can support the ends 1080A/B of the aperture 350 and prevent the aperture 350 from closing when the valve 10 is transitioning from the closed mode to the open mode.

In operation, as the medical practitioner 20 inserts the medical implement 40 and begins to move the instrument 40 distally, the actuator 330 and the stationary leg members 1010 deform the proximal portion 1030 of the resilient member 340 into the gap 1060 between the proximal portion 1030 and the distal portion 1040. As the proximal portion 1030 deforms, the cooperation between the stationary legs 1010 and the protrusions 1070 A, B, C, and D begins to open the aperture 350. As mentioned above, the taller protrusions 1070A and 1070C, which are located beneath the ends 1080A/B of the aperture 350, support the ends 1080A/B and prevent them from closing as the valve 10 is opening. In particular, as the stationary leg members 1010 begin to deform the resilient member 340 and the stationary leg members 1010 and the protrusions 1070 A, B, C, and D cooperate to open the sides of the aperture 350, the ends 1080A and B begin to close inwardly and begin to close the aperture 350. The taller protrusions 1070A and 1070C prevent the ends from closing inwardly in this manner. In some embodiments, the taller protrusions 1070A and 1070C may extend into the aperture 350 when open.

The above described embodiments describe medical valves with either moveable leg members 360 or stationary leg members 1010. However, as shown in FIGS. 11A-11E, some embodiments of the present invention can include a combination of stationary leg members 1010 and moveable leg members 360. In particular, some embodiments may include moveable leg members 360 located on either side of the aperture 350 (see FIG. 11B) and stationary leg members 1010 located at each aperture end 1080A/B (see FIG. 11A). The moveable leg members 360 act to open the aperture 350, while the stationary members 1010 prevent the ends 1080A/B from closing inwardly as the valve opens.

Figure 11A:
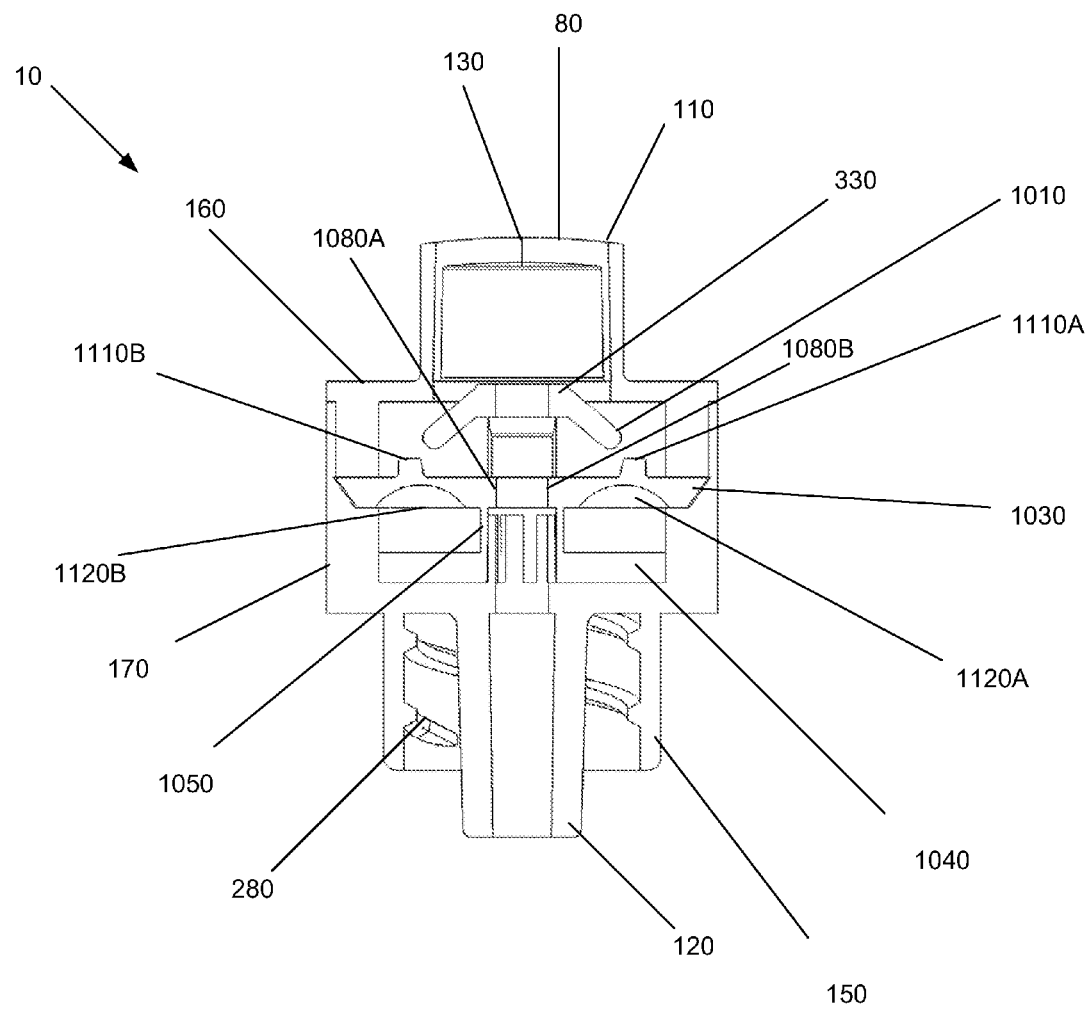
FIG. 11A schematically shows a front cross-sectional view of an alternative embodiment having two stationary and two moveable leg members. This figure shows the stationary leg members, a moveable leg member, and the valve in the closed mode.
Figure 11B:
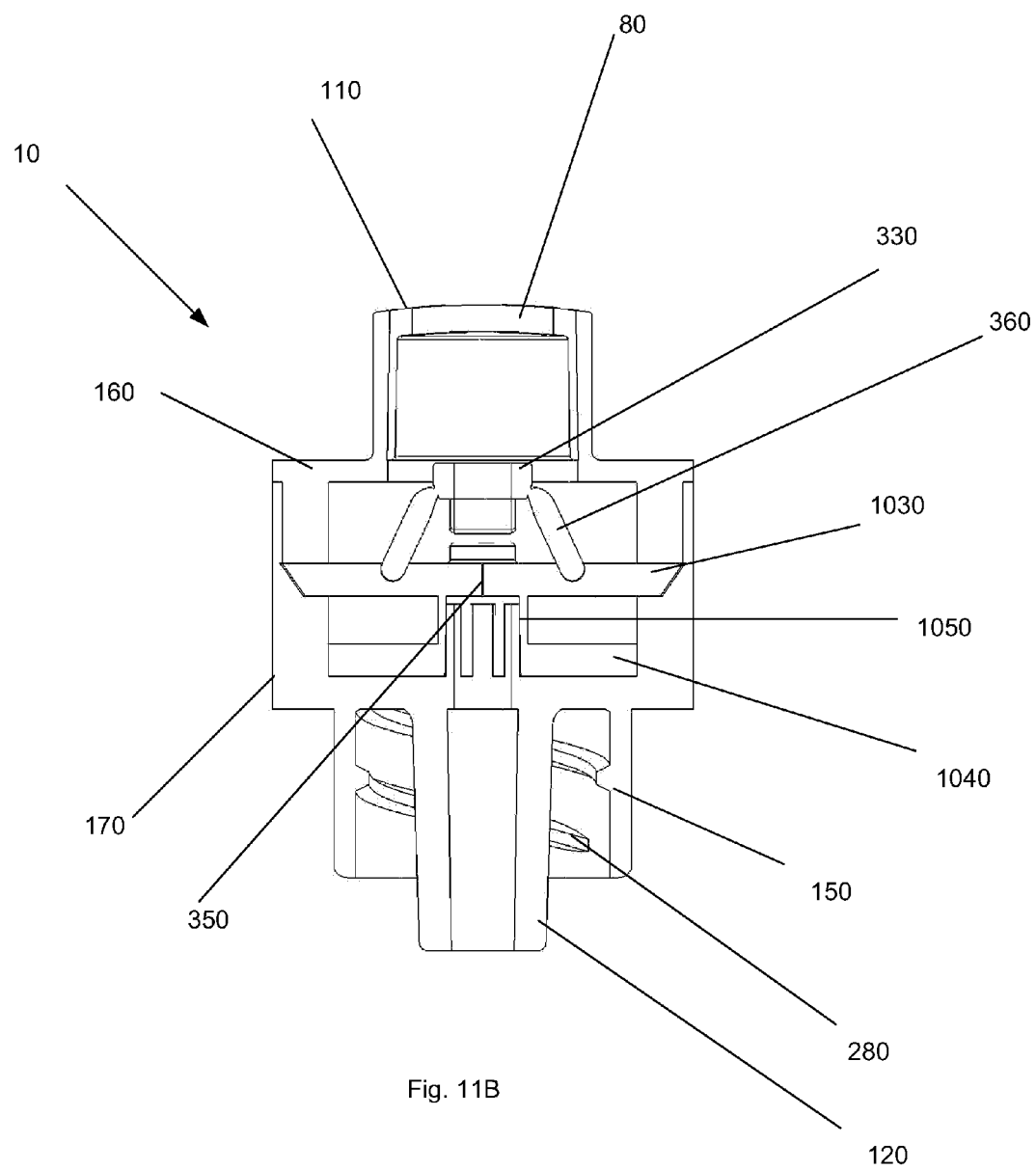
FIG. 11B schematically shows a side cross-sectional view of the alternative embodiment shown in FIG. 11A. This figure shows the moveable leg members and the valve in the closed mode.
Figure 11C:
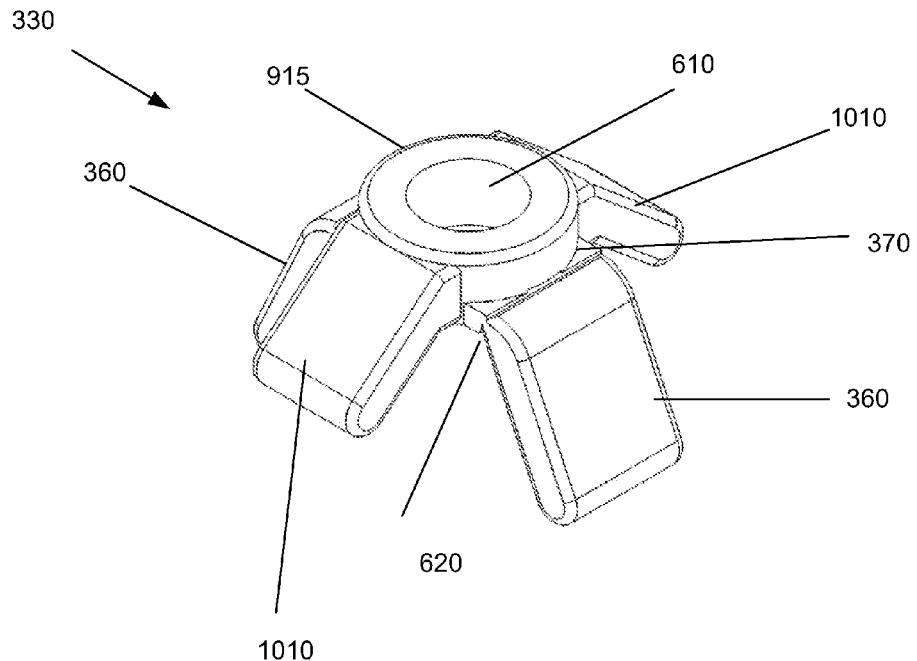
FIG. 11C schematically shows an illustrative embodiment of the actuator within the valve of FIG. 11A and 11B.
Figure 11D:
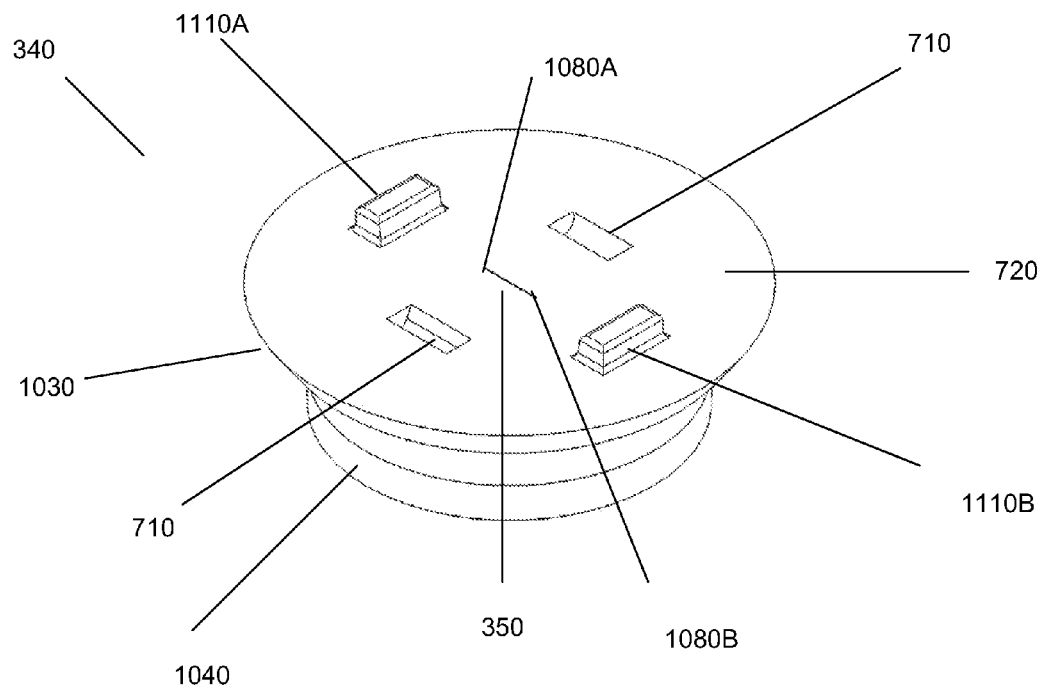
FIG. 11D schematically shows an illustrative embodiment of the resilient member within the valve of FIG. 11A and 11B.

As shown in FIG. 11D, the resilient member 340 has a very similar structure to that described above with reference to 10D and 10E. In some embodiments, the resilient member can be sized so that the outer diameter is larger than the inner diameter of the outlet housing 170. By sizing the components this way, the outlet housing 170 will apply a radially compressive force to the resilient member 340 when the valve is assembled. This radially compressive force will force the sides of the aperture 350 to remain closed when the valve 10 is in the closed mode. Additionally, because radial compression applied to the aperture ends 1080A/B would act to open the aperture, the resilient member may have thinned sections 1120A/B (FIG. 11A) located at either aperture end 1080A/B. The thinned sections 1120A/B relieve some of the radial compressive forces applied to the aperture ends 1080A/B so that the aperture 350 remains closed.

The resilient member 340 may also include resilient member protrusions 1110A/B. As described in more detail below, the resilient member protrusions 1110A/B cooperate with the stationary leg members 1010 to prevent the aperture ends 1080A/B from closing inwardly as the sides expand outwards.

Figure 11E:
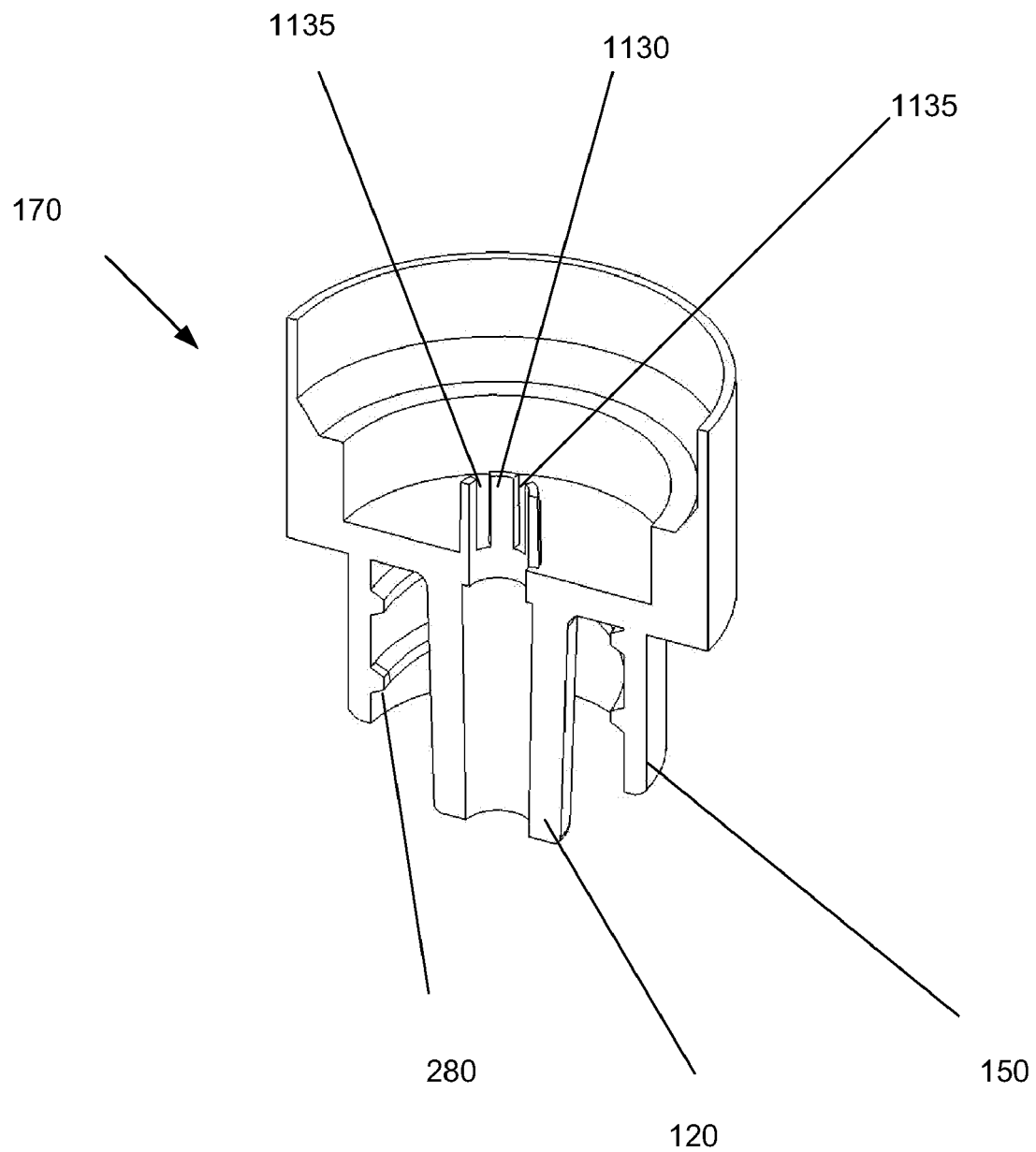
FIG. 11E schematically shows a cross sectional view of the outlet of the alternative embodiment shown in 11A FIG. 12A schematically shows a front cross-sectional view an alternative embodiment having an actuator with a distally extending portion and a resilient member having a proximally extending portion. This figure shows the valve in the closed mode.

As shown in FIG. 11E, the outlet 170 may also have a center post member 1130 protruding proximally. The center post member 1130 aids in the opening of the aperture by providing proximally directed resistance around the aperture as the resilient member 340 deforms distally. Although the center post member 1130 can be a substantially uninterrupted structure, it may also have center post channels 1135 that interrupt the structure of the center post member 1130. The center post channels 1135 improve valve flushing.

In operation, as the medical practitioner 20 moves the instrument 40 (and therefore the actuator 330) distally, the moveable leg members 360 begin to flex outwardly and apply a force to the sides of the aperture 350, opening the aperture 350. As the actuator moves further, the stationary leg members 1010, which may be shorter than the moveable leg members 360, engage the resilient member protrusions 1110A/B. Once engaged, the resilient member protrusions 1110A/B and stationary leg members 1010 cooperate to prevent the aperture ends 1080A/B from closing inwardly as the sides of the aperture 350 expand outwardly.

Figure 12A:
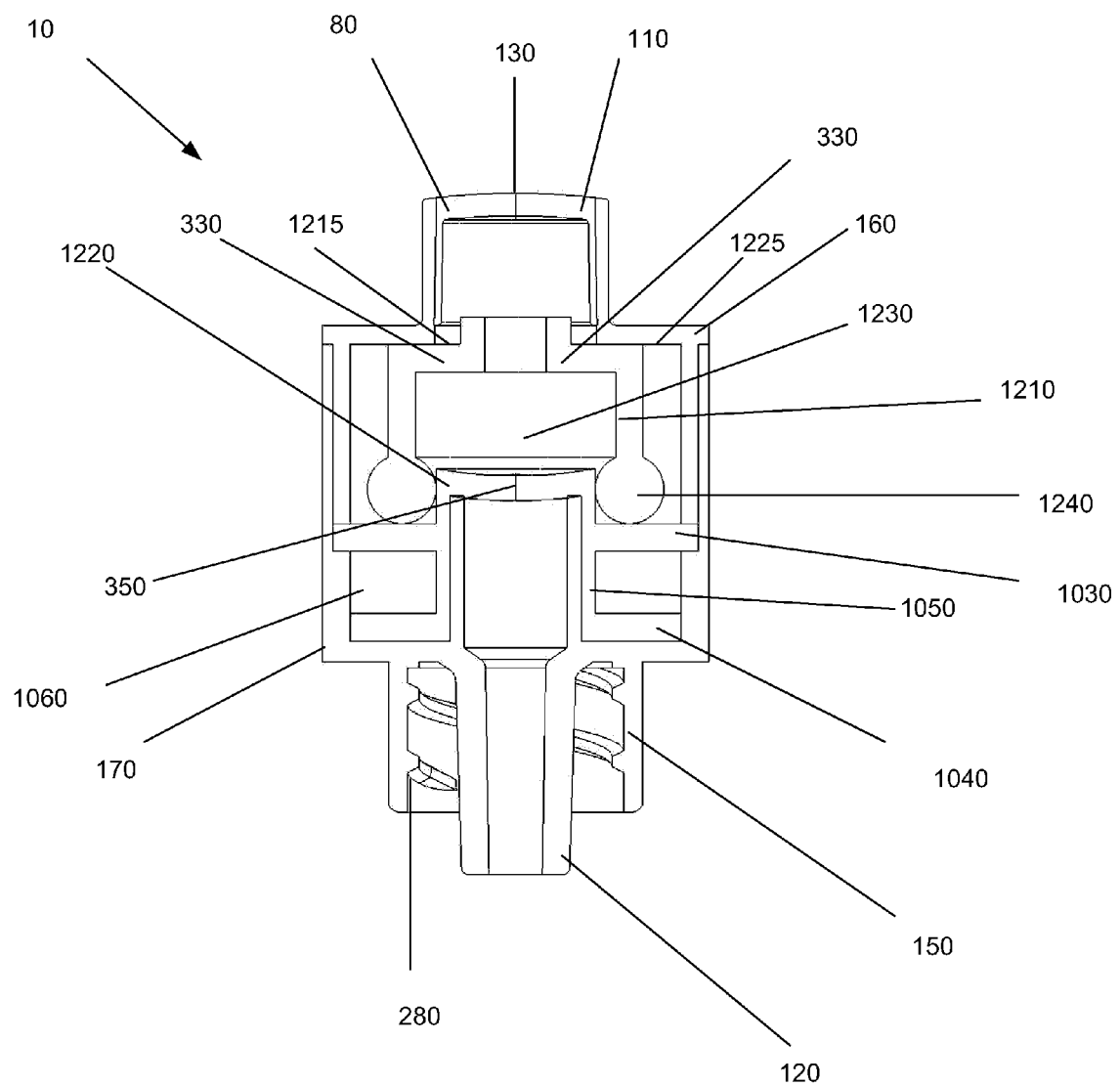
FIG. 12B schematically shows a perspective exploded view of the medical valve shown in FIG. 12A.
Figure 12B:
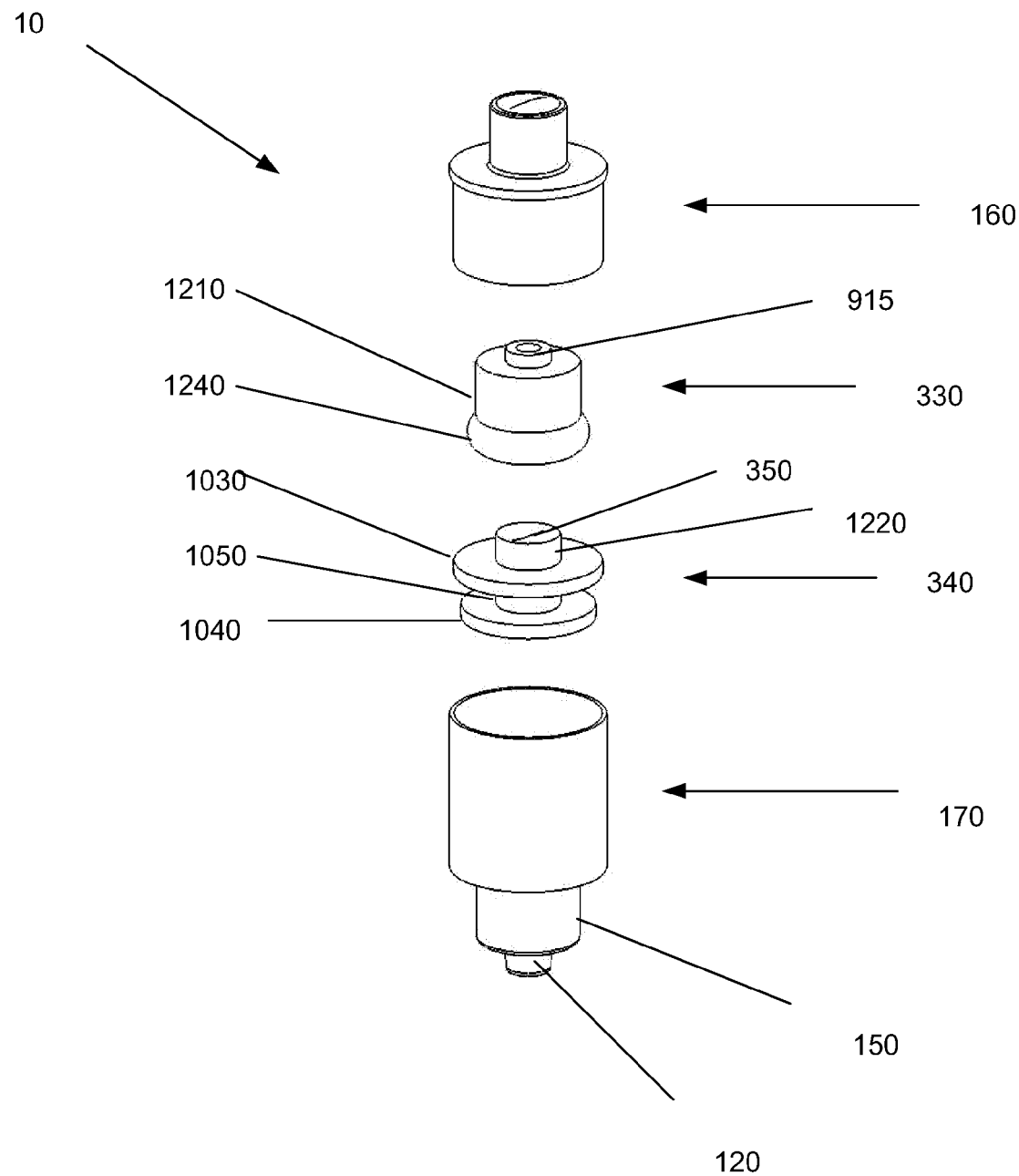

FIGS. 12A and 12B schematically show another embodiment of the medical valve in which the actuator 330 provides a radially compressive force to the resilient member 340 to keep the aperture 350 closed when the valve 10 is in the closed mode. The radially compressive force also improves the valve's ability to withstand backpressure. To that end, the actuator 330 has a distally extending portion 1210 that cooperates with a proximally extending portion 1220 of the resilient member 340.

As shown in FIGS. 12A and 12B, the resilient member 340 can have a structure similar to that described above with respect to FIGS. 10A through 10F. In particular, the resilient member can have a proximal portion 1030, a distal portion 1040, and an intermediate portion 1050. The proximally extending portion 1220 can extend proximally from the proximal portion 1030.

The distally extending portion 1210 of the actuator 330 can be any number of structures that are capable of applying a radially compressive force to the proximally extending portion 1220 of the resilient member 340. For example, the distally extending portion 1210 can be a skirt or a set of leg members similar to those described above. In either scenario, the distally extending portion 1210 may sit over the proximally extending portion 1220 such that the proximally extending portion 1220 extends into the space 1230 within the skirt/distally extending portion 1210. The distally extending portion 1210 may also include an enlarged portion 1240. The enlarged portion 1240 ensures that sufficient radially compressive force is applied to the aperture 350 when the valve is in the closed mode. Additionally, if the enlarged portion 1240 is spherical (as shown in FIGS. 12A and 12B), the enlarged portion 1240 will have a minimal contact area with the resilient member 340.

As the valve transitions from the open mode to the closed mode and the actuator 330 begins to move distally, the proximal surface 1030 of the resilient member 340 will begin to deform into space 1060. Additionally, the proximally extending portion 1220 will begin to deform into the space 1230 within the distally extending portion 1210. As the proximally extending portion 1220 begins to deform, the aperture 350 will open into the space 1230 (e.g., the material at the sides of the aperture 350 will deform proximally into the space 1230).

In some embodiments, a body portion proximal surface 1215 of the actuator 330 can contact an inner surface 1225 of the inlet housing 160. The interaction between the body portion proximal surface 1215 and the inner surface 1225 of the inlet housing 160 keep the actuator 330 in place when the valve 10 is in the closed mode (e.g., the interaction prevents the actuator 330 from moving within the interior of the housing 100). In some embodiments, the interaction may also create a pre-load on the resilient member (e.g., the actuator 330 and the inlet housing 160 may be sized such that there is a distally directed force on the resilient member 340).

Figure 13A:
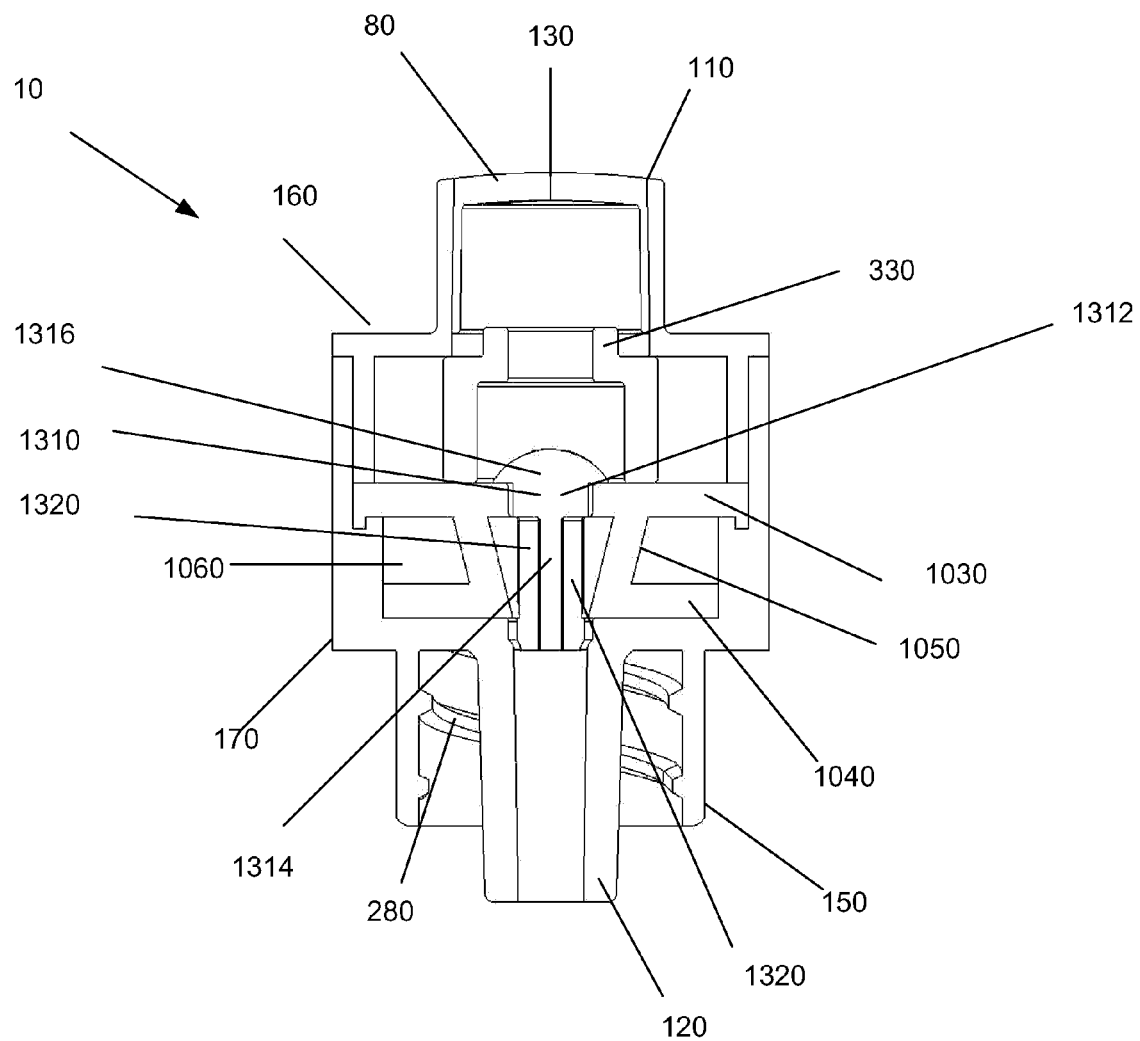
FIG. 13A schematically shows a front cross-sectional view an alternative embodiment having a proximally extending post member. This figure shows the valve in the closed mode.

As shown in FIGS. 13A through 13C, some embodiments of the present invention can include a plug member 1310 that extends proximally from the outlet 170. The plug member 1310 may pass through the aperture 350 and cooperate with the resilient member 340 to prevent flow through the valve 10, when the valve 10 is in the closed mode. In particular, the plug member 1310 may have a proximal portion 1312 that is proximal to the resilient member 340 and a distal portion 1314 that is distal to the resilient member 340. In some embodiments, the proximal portion 1312 may be "o-shaped" and the resilient member can seal against the outer diameter of the "o-shaped" portion. In other embodiments, the plug member 1310 can have a button top 1316 against which the resilient member can seal.

As the valve transitions from the closed mode to the open mode, the actuator 330 will deform the resilient member 340 and unseal the resilient member 340 from the plug member 1310. By deforming the resilient member 340, the actuator 330 will create fluid communication between the proximal port 110 and the distal port 120 through a series of plug member channels 1320 located on the distal portion 1314 of the plug member 1310.

Figure 14:
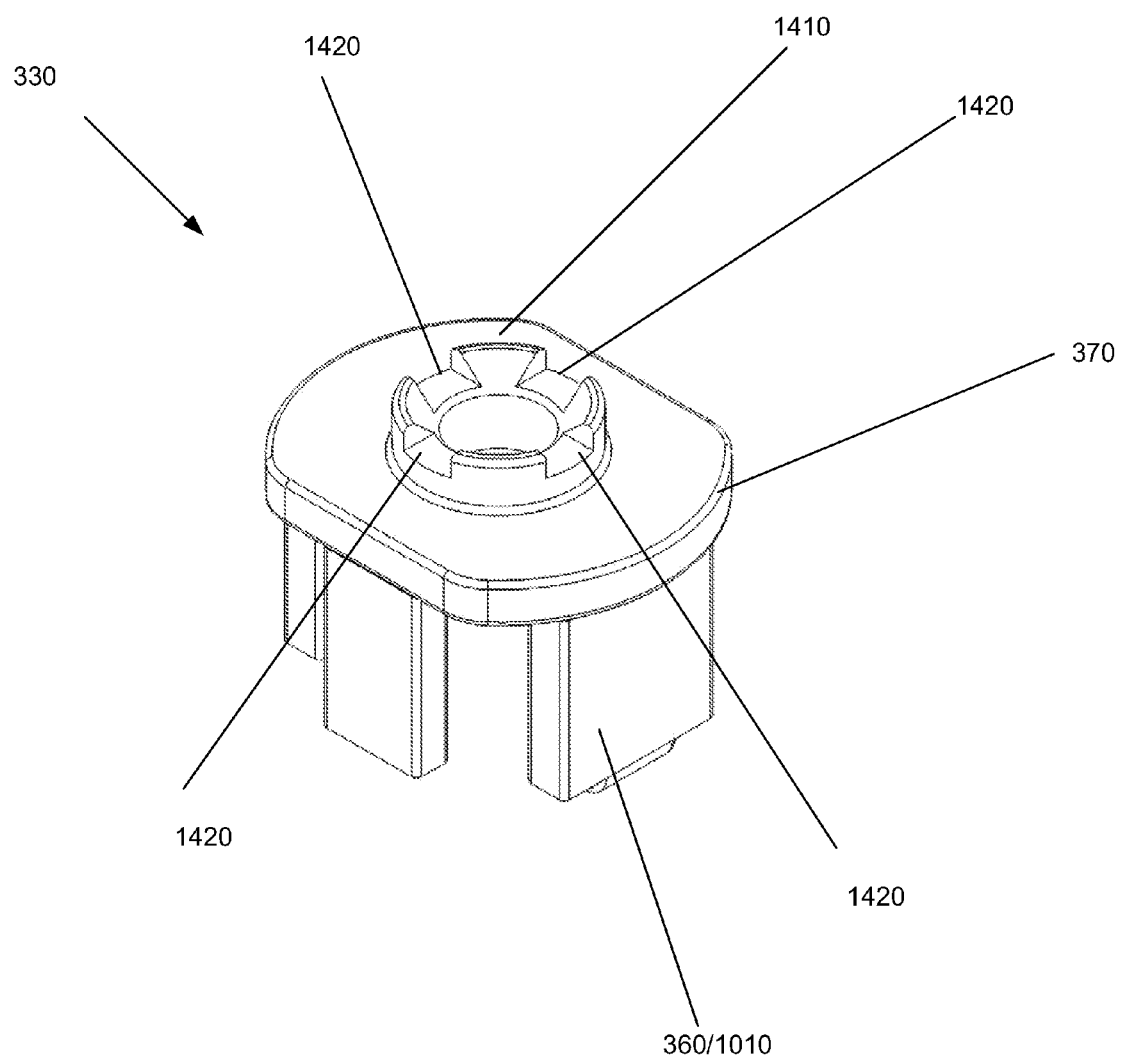
FIG. 14 schematically shows an alternative embodiment of an actuator with improved flushing. This alternative actuator can be used in conjunction with any of the above shown medical valves.

As shown in many of the above described figures, the actuator may have a raised contact surface 915 that is substantially uninterrupted (e.g., no channels or grooves). However, as shown in FIG. 14, the actuator 330 may have an interrupted contact surface 1410 having channels 1420 to improve flushing. The channels may extend radially outward from the center of the contact surface 1410. Alternatively, if the proximal surface of the actuator 330 does not have a raised contact surface 915, the channels can be located on the actuator's proximal surface.

Although the above discussion discloses various exemplary embodiments of the invention, it should be apparent that those skilled in the art can make various modifications that will achieve some of the advantages of the invention without departing from the true scope of the invention.

What is claimed is:

1. A medical valve having an open mode that permits fluid flow, and a closed mode that prevents fluid flow, the medical valve comprising:
a housing having an inlet and an outlet;
an actuator moveable distally within the housing after insertion of a medical implement into the inlet, the actuator having a body portion and a plurality of leg members extending from the body portion; and
a resilient member having a normally closed aperture, wherein distal movement of the actuator opens the aperture thereby transitioning the valve from the closed to the open mode, the leg members interacting with the resilient member to open the aperture, the distal movement of the actuator causing the plurality of leg members to apply a radial force on the aperture to open the aperture;

wherein the plurality of leg members are connected to the body portion by a hinge such that the plurality of leg members are movable with respect to the body portion, and wherein the plurality of leg members move generally radially outward as the actuator moves distally thereby applying the radial force on the aperture and opening the aperture.

2. A medical valve according to claim 1, wherein the resilient member proximally biases the actuator.

3. A medical valve according to claim 1, wherein proximal movement of the actuator closes the aperture thereby transitioning the valve from the open to the closed mode.

4. A medical valve according to claim 1, wherein the aperture is a slit.

5. A medical valve according to claim 1, further comprising a second plurality of leg members substantially stationary with respect to the body portion.

6. A medical valve according to claim 1, wherein the actuator further comprises:

a plurality of stationary leg members extending from the body portion, the stationary members being substantially stationary with respect to the body portion.

7. A medical valve according to claim 6, wherein the resilient member includes a plurality of protrusions, the plurality of stationary members engaging the protrusions as the valve transitions from the closed mode to the open mode thereby preventing the aperture from closing.

8. A medical valve according to claim 1 further comprising a valve seat, wherein the resilient member seals against the valve seat.

9. A medical valve according to claim 8, wherein the valve seat is angled such that the resilient member deforms to the shape of the valve seat as the valve transitions from the closed to the open mode.

10. A medical valve according to claim 1 further comprising a swabbable member sealing the inlet.

11. A medical valve according to claim 1, the housing further comprising a plurality of protrusions extending proximally from the outlet and configured to prevent the aperture from closing as the valve transitions from the closed mode to the open mode.

12. A medical valve according to claim 1, wherein the aperture is self-sealing.

13. A medical valve according to claim 1, wherein the actuator includes an actuator channel through the actuator.

14. A medical valve according to claim 1, wherein a positive fluid displacement occurs at the outlet during withdrawal of the medical implement.

15. A medical valve according to claim 1, wherein a substantially neutral fluid displacement occurs at the outlet during withdrawal of the medical implement.

16. A medical valve according to claim 1, wherein the aperture is a pinhole.

17. A medical valve according to claim 1, wherein the actuator and the resilient member are chemically bonded to one another to form a single internal valve mechanism.

18. A medical valve according to claim 1, wherein the actuator and the resilient member are formed using a two-shot manufacturing process, thereby creating a single internal valve mechanism.

19. A medical valve according to claim 1, wherein the plurality of leg members remain exterior to the aperture as the aperture opens.

20. A method comprising:

connecting a medical valve to a patient, the medical valve comprising:

a housing having an inlet and an outlet;

an actuator moveable distally within the housing after insertion of a medical implement into the inlet, the actuator having a body portion and a plurality of leg members extending from the body portion; and a resilient member having a normally closed aperture, wherein distal movement of the actuator opens the aperture thereby transitioning the valve from the closed to the open mode, the leg members interacting with the resilient member to open the aperture, the distal movement of the actuator causing the plurality of leg members to apply a radial force on the aperture to open the aperture;

wherein the plurality of leg members are connected to the body portion by a hinge such that the plurality of leg members are movable with respect to the body portion, and wherein the plurality of leg members move generally radially outward as the actuator moves distally thereby applying the radial force on the aperture and opening the aperture;

inserting a medical implement through the inlet to contact the actuator;

moving the medical implement distally within the housing to move the actuator distally until the actuator opens an aperture within the resilient member such that the inlet and the outlet are in fluid communication; and transferring fluid between the medical implement and the patient through the valve.

21. The method according to claim 20 wherein the valve forms a fluid channel between the inlet and the outlet when the actuator opens the aperture, the fluid channel being substantially longitudinally directed.

22. The method according to claim 20 wherein the resilient member proximally biases the actuator, the proximal biasing causing the aperture and valve to be in a normally closed mode that prevents fluid flow through the valve.

23. The method according to claim 20 wherein the medical implement is a syringe having a standard luer taper at its distal end.

24. The method according to claim 20 wherein transferring comprises injecting fluid from the medical implement to the patient.

25. The method according to claim 20 wherein transferring comprises removing fluid from the patient.

26. A method according to claim 20, further comprising a second plurality of leg members substantially stationary with respect to the body portion.

27. A method according to claim 20, wherein the valve includes a valve seat that creates a seals against the resilient member.

28. A method according to claim 20, wherein the valve seat is angled such that the resilient member deforms to the shape of the valve seat as the valve transitions from the closed to the open mode.

29. A method according to claim 20 further comprising producing a positive fluid displacement through the outlet after inserting the medical implement into the inlet.

30. A method according to claim 20 further comprising producing a substantially neutral fluid displacement when withdrawing the medical implement.

31. A medical valve having an open mode that permits fluid flow, and a closed mode that prevents fluid flow, the medical valve comprising:

a housing having an inlet and an outlet;

actuating means moveable distally within the valve after insertion of a medical implement into the inlet, the actuating means having a plurality of leg members extending from a body portion; and a resilient member having a normally closed aperture, wherein distal movement of the actuating means opens the aperture thereby transitioning the valve from the closed to the open mode, the aperture fluidly communicating the inlet and the outlet when open, the plurality of leg members interacting with the resilient member to open the aperture, the distal movement of the actuating means causing the plurality of leg members to apply a radial force on the aperture to open the aperture;

wherein the plurality of leg members are connected to the body portion by a hinge such that the plurality of leg members are movable with respect to the body portion, and wherein the plurality of leg members move generally radially outward as the actuator moves distally thereby applying the radial force on the aperture and opening the aperture.

32. A medical valve according to claim 31, wherein the resilient member proximally biases the actuating means, proximal movement of the actuating means closes the aperture.

33. A medical valve according to claim 31, further comprising a second plurality of leg members substantially stationary with respect to the body portion.

34. A medical valve according to 31, wherein a second set of a plurality of leg members are substantially stationary with respect to the body portion.

35. A medical valve according to claim 31, further comprising a valve seat, wherein the resilient member seals against the valve seat.

36. A medical valve according to claim 35, wherein the valve seat is angled such that the resilient member deforms to the shape of the valve seat as the valve transitions from the closed mode to the open mode.

* * * * *